US012796994B2

(12) United States Patent

Ophir et al.

(10) Patent No.: US 12,796,994 B2

(45) Date of Patent: Nov. 17, 2026

(54) MACHINE LEARNING (ML)-BASED DISEASE-DETECTION SYSTEM USING DETECTION ANIMALS

(71) Applicant: Spotitearly Ltd.

(72) Inventors: Roi Ophir, Tel Aviv (IL); Ohad Sharon, Hamaapil (IL); Assaf Rabinowicz, Bat-Yam (IL); Udi Bobrovsky, Saad (IL); Reef Einoch Amor, YoKne'am Illit (IL); Amir Lifshitz, Kibutz Hama'apil (IL)

(73) Assignee: Spotitearly Ltd. (IL)

( * ) Notice: Subject to any disclaimer, the term of this patent is extended or adjusted under 35 U.S.C. 154(b) by 276 days.

(21) Appl. No.: 18/331,144

(22) Filed: Jun. 7, 2023

(65) Prior Publication Data

US 2024/0260880 A1 Aug. 8, 2024

Related U.S. Application Data

(60) Provisional application No. 63/482,979, filed on Feb. 2, 2023, provisional application No. 63/350,372, filed on Jun. 8, 2022.

(51) Int. Cl.

| | |
|---|---|
| ***A01K 15/02*** | (2006.01) |
| ***A61B 5/316*** | (2021.01) |
| ***G16B 40/00*** | (2019.01) |
| ***G16H 50/20*** | (2018.01) |

(Continued)

(52) U.S. Cl.

CPC .............. *A61B 5/316* (2021.01); *G16B 40/00* (2019.02); *G16H 50/20* (2018.01); *G16H 50/30* (2018.01); *G01N 33/497* (2013.01)

(58) Field of Classification Search

None

See application file for complete search history.

(56) References Cited

U.S. PATENT DOCUMENTS

| | | | | |
|---|---|---|---|---|
| 5,120,643 | A | 6/1992 | Ching | |
| 11,583,604 | B1 * | 2/2023 | Gressick | A61L 9/02 |
| 2009/0057259 | A1 | 3/2009 | Johnson | |

(Continued)

FOREIGN PATENT DOCUMENTS

| | | | | |
|---|---|---|---|---|
| WO | WO-2021188992 A1 * | 9/2021 | | A01K 15/02 |
| WO | WO-2022015700 A1 * | 1/2022 | | A61B 5/7267 |

OTHER PUBLICATIONS

International search report and Written Opinion received for PCT Application No. PCT/US23/24785, 40 pages, Oct. 12, 2023.

(Continued)

*Primary Examiner* — James Kish

(74) *Attorney, Agent, or Firm* — Baker Botts L.L.P.

(57) ABSTRACT

In one embodiment, a system for disease-detection includes a machine learning-based (ML-based) disease-detection model trained on a dataset of detection events, wherein one or more ML-models is operable to receive sensor data associated with one or more detection animals that have been exposed to a biological sample of a patient, process the sensor data to generate one or more feature representations, and calculate, based on the one or more feature representations, one or more confidence scores corresponding to one or more disease states associated with the biological sample, wherein each confidence score indicates a likelihood of the respective disease state being present in the patient.

30 Claims, 26 Drawing Sheets

(51) Int. Cl.

| | |
|---|---|
| ***G16H 50/30*** | (2018.01) |
| *G01N 33/497* | (2006.01) |

(56) References Cited

U.S. PATENT DOCUMENTS

| | | | | |
|---|---|---|---|---|
| 2009/0211581 | A1 | 8/2009 | Bansal | |
| 2015/0157273 | A1 | 6/2015 | An | |
| 2015/0301021 | A1 | 10/2015 | Haick | |
| 2016/0171682 | A1 | 6/2016 | Abedini | |
| 2016/0345539 | A1 | 12/2016 | Mark-Danieli | |
| 2017/0261478 | A1* | 9/2017 | Stokes | G01N 33/0001 |
| 2018/0293430 | A1* | 10/2018 | Datta | A01K 29/005 |
| 2021/0055267 | A1 | 2/2021 | Zhang | |
| 2021/0298661 | A1* | 9/2021 | Smith | A61B 5/4011 |
| 2022/0061823 | A1 | 3/2022 | Berger | |
| 2022/0087220 | A1* | 3/2022 | Kjellsen | A01K 15/021 |
| 2022/0095948 | A1 | 3/2022 | Mitchell | |
| 2022/0125333 | A1* | 4/2022 | Alburty | A61B 5/097 |
| 2023/0062575 | A1* | 3/2023 | Mark Danieli | A01K 15/02 |

OTHER PUBLICATIONS

Withington, et al., "Artificial neural networks for classifying the time series sensor data generated by medical detection dogs", expert systems with applications Elsevier, Amsterdam, NL, vol. 184, 115564, 13 pages, Jul. 10, 2021.

Erez, et al., "A mouse bio-electronic nose for sensitive and versatile chemical detection", 22 pages, May 8, 2020.

Li, et al., "Wearable Sensors for Canine Nosework Sniffing Interaction", Eight International Conference On Animal-Computer Interaction Acmpub27, New York, 8 pages, Nov. 8, 2021.

* cited by examiner

1900

2100

2200

INTERIM RESULTS | EXPLORATORY CANCER TYPES

8 EXPLORATORY CANCER TYPES.

DETECTED WITH 80% SENSITIVITY,

WITHOUT SPECIFIC TRAINING.

| CANCER TYPE | CANCER FREQUENCY | SENSITIVITY |
|---|---|---|
| KIDNEY | 9/11 | 81.82% |
| BLADDER | 8/9 | 88.89% |
| OVARIAN CANCER | 5/7 | 71.43% |
| CERVIX | 4/4 | 100% |
| STOMACH | 2/2 | 100% |
| TYPICAL CARCINOID/ ENDOMETRIOID CARCINOMA | 3/4 | 75% |
| PANCREAS/ PANCREAS ADENOCARCINOMA | 2/2 | 100% |
| VULVA | 1/1 | 100% |

*FIG. 22*

MACHINE LEARNING (ML)-BASED DISEASE-DETECTION SYSTEM USING DETECTION ANIMALS

PRIORITY

This application claims the benefit under 35 U.S.C. § 119(e) of U.S. Provisional Patent Application No. 63/350,372, filed 8 Jun. 2022, and also claims the benefit under 35 U.S.C. § 119(e) of U.S. Provisional Patent Application No. 63/482,979, filed 2 Feb. 2023, each of which is incorporated herein by reference.

TECHNICAL FIELD

This disclosure relates generally to medical diagnostics using a system of signal analysis of detection animals.

BACKGROUND

People undergo medical screening for a variety of reasons, including screening tests as part of a general health screening or diagnostic tests to detect for specific conditions. For many diseases, patient outcomes improve significantly if the disease is detected early. Accordingly, there are many screening and diagnostic tests which attempt to detect diseases such as various cancers, heart disease, and other medical conditions. Presently, most diagnostic tests require point-of-care visits, which require a patient to be at a medical facility. Alternatively, some tests require a professional nurse to travel to a patient's home to take measurements. Furthermore, most tests are performed due to a patient exhibiting a particular symptom, and most tests scan for a specific outcome. Due to the above, screening and diagnostic tests today are expensive, intrusive, lack test sensitivity, and require a large time commitment by both the healthcare system and the patient. As a result, adherence to various tests and the willingness of people to adopt them is not high.

There are many screening and diagnostic tests for cancer detection. Example tests include liquid biopsy, which is not only expensive and requires point-of-care specimen collection, but also has low sensitivity to detecting cancer at its early stages. Another example cancer detection procedure is by nematode-based multi-cancer early detection (N-NOSE), which is performed by collecting a patient's urine sample. Many cancer screens detect a limited number of types of cancer and require a separate screening procedure for each cancer. These cancer screens are expensive, inconvenient, invasive, and require point-of-care settings which require a substantial time commitment. Further, these cancer screens lack sensitivity or result in high false positive rates. Moreover, laboratories have a limited capacity to perform these tests and patients have a low adherence rate in properly preparing for these tests. Thus, there is a need for medical diagnostic and screen tests which have high sensitivity, are non-invasive, non-expensive, efficient, and capable of detecting many different diseases.

Many physiological processes, including diseases such as cancer, produce detectable odorants which animals may be trained to detect. For example, cancers produce volatile organic compounds (VOCs) which are excreted into the blood, sweat, saliva, urine, and breath of people with cancer. VOCs are a crucial, early indication of cancer. Traditional diagnostic devices are unable to perform cancer detection using VOC monitoring due, in part, to the low concentrations of cancerous VOCs and a low signal-to-noise ratio.

However, VOCs produce a distinctive odor profile which are detectable by canines and other animals. Further, different types of cancer have unique VOC signatures which may be identified by trained animals.

Additionally, certain bacterial or viral infections produce unique scent profiles in living organisms such as humans and animals. These odorants are typically released from humans through breath, urine, feces, skin emanations, and blood, and may be detectable by animals with strong olfactory abilities.

Canines have extremely sensitive olfactory receptors and are able to detect many scents that a human cannot. Canines can pick out specific scent molecules in the air, even at low concentrations. Further, canines may be trained to perform a certain act, such as sitting down, upon detection of a target odor. Additionally, rodents, fruit flies, and bees also have high olfactory capabilities and may be trained to detect specific scents.

The present embodiments described herein are directed to a disease-detection system which tracks the behavioral, physiological and neurological patterns of detection animals in a controlled environment and uses those signals to enhance, verify and increase the accuracy of medical diagnostics. Benefits of the disclosed systems and methods include having high accuracy in high throughput screening and diagnostic laboratory tests resulting in early detection of cancer or cancer remission. In particular, early identification of cancer may reduce the need for more invasive procedures such as biopsies. The system may also improve treatment monitoring by enabling more frequent screenings. The system may also provide cancer survivors with easy, cost-effective, and frequent screenings. Further, the system allows for the screen of large populations to identify positive or high-risk individuals. Additionally, the system ensures high accuracy in interpreting animals' behavior.

The embodiments disclosed herein are only examples, and the scope of this disclosure is not limited to them. Particular embodiments may include all, some, or none of the components, elements, features, functions, operations, or steps of the embodiments disclosed herein. Embodiments according to the invention are in particular disclosed in the attached claims directed to a method, a kit, and a system, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

BRIEF DESCRIPTION OF THE DRAWINGS

FIG. 4 illustrates an example sample collection protocol.

FIG. 22 depicts experimental results.

DESCRIPTION OF EXAMPLE EMBODIMENTS

Disease-Detection System Overview

In particular embodiments, a disease-detection system for detection animals for medical diagnostics may comprise a combination of sensors, cameras, operational systems, and machine learning (ML) algorithms, which may serve one or more of the following purposes: (1) real-time management of the screening tests in the lab, which include presenting the test's setting and events in real-time on the lab manager's monitor or guiding the lab manager on how to operate the test based on the test protocol, (2) management of the testing facility's resources and clients, including patients, samples, canines, handlers, and lab managers, (3) management of monitoring and analytics which support training plans of detection animals, (4) management of communications with the customer, the customer's healthcare provider(s), third parties, and the screening centers, including customer subscriptions, sample shipping, payment, and laboratory results communication, in both direct-to-consumer and business-to-business-to-consumer scenarios, (5) collecting and synchronizing data from different sources and providing raw data to the testing facility, (6) providing test data in real-time to the disease-detection system, (7) providing analytical-based recommendations for lab results, including a positive/negative test result and a confidence score, at difference stages of the testing process, (8) a real-time monitoring and alerting system, which ensures the quality of the testing facility's product and resources, as well as alerts whenever an anomaly is detected, (9) identification of the type of cancer present or the cancer stage in a biological sample by analyzing the detection animal's brain imaging (e.g. from an EEG, fNIR, fMRI, or MRI), or (10) using the detection animal's brain imaging as a verification step.

The system tracks and monitors hundreds of signals at every second produced in real time by detection animals (e.g., cancer-sniffing dogs) as the detection animals are exposed to the samples in the laboratory and combine the signals with medical data. The result is an accurate, non-invasive, and fast screening test for one or more disease states (e.g., cancer), with a higher level of sensitivity than devices or screening tests which are used in medicine today.

Figure 1:
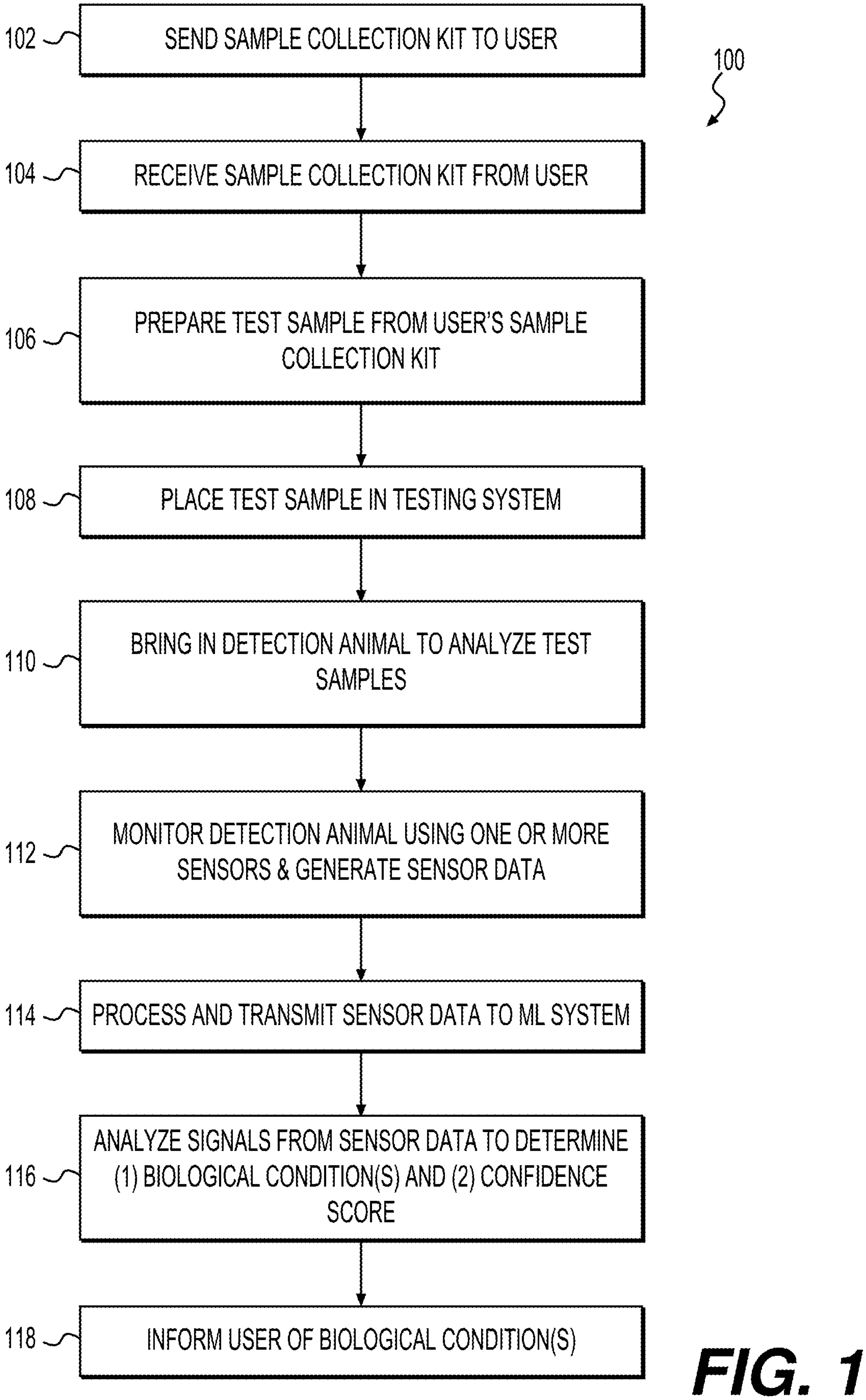
FIG. 1 illustrates an example disease-detection method.

FIG. 1 illustrates a flow diagram of a method 100 for a disease-detection system in accordance with the presently disclosed embodiments. The method 100 may be performed utilizing one or more processing devices that may include hardware, e.g., a general purpose processor, a graphic processing unit (GPU), an application-specific integrated circuit (ASIC), a system-on-chip (SoC), a microcontroller, a field-programmable gate array (FPGA), a central processing unit (CPU), an application processor (AP), a visual processing unit (VPU), a neural processing unit (NPU), a neural decision processor (NDP), or any other processing device(s) that may be suitable for processing sensor data, software (e.g., instructions running/executing on one or more processors), firmware (e.g., microcode), or some combination thereof. In particular embodiments, the disease-detection system comprises one or more ML-models (e.g., a ML-based disease-detection model). The disease-detection system may further comprise one or more additional computing components, including a monitoring component and an operational component.

The method 100 may begin at step 102 with the testing facility, either directly or through an affiliate, sending a sample collection kit to a user after receiving a request from a user (e.g., a patient) or the user's physician. In particular embodiments, a customer ID is assigned to the user and the customer ID is associated with the user's biological sample through the life cycle of the biological sample. In particular embodiments, a physician may order a general screening test. In other embodiments, a physician may order a diagnostic test for one or more diseases in response to the user communicating the presence of particular symptoms. In particular embodiments, the sample collection kit comprises a collection device and user instructions. In particular embodiments, the collection device may be a facial mask or a surgical mask that the user breathes into for a specified amount of time. In particular but non-limiting embodiments, the collection device may be a tube, a cup, a bag, or any suitable collection kit which may be used to collect a biological sample. As an example and not by way of limitation, in a particular embodiment, the user receives a collection device and is instructed to breathe into the collection device for five minutes. As an example and not by way of limitation, the sample collection may be performed from home, at a survey institute, at a clinic, or any other location suitable for sample collection. The full life cycle of the sample, from activation to extermination, is tracked with a high level of traceability.

The method 100 may then continue at step 104 with the test facility receiving the sample collection kit from the user. Upon receipt of the sample collection kit, the test facility processes the kit by labeling the sample with an identification number corresponding to the user and enters information related to the received sample into the disease-detection system. In particular embodiments, the disease-detection system may contain information about the user, such as name, age, prior health history, family health history, lifestyle habits, etc.

The method 100 may then continue at step 106 with a person or a machine preparing a biological sample from the user's sample collection kit. In particular embodiments, a person or a machine performs a method of extracting chemical molecules out of the biological sample. In particular embodiments, a lab worker may open the collection device, e.g. a mask, and split the mask into two or more parts so that there is at least a biological sample (test sample) and a backup sample. In particular embodiments, one of the parts of the biological sample may be used for testing by traditional methods, such as by gas chromatography mass spectrometry (GCMS) or biopsy. In particular embodiments, the lab worker may put the biological sample into a receptacle operable to be attached to an olfactometer. In particular embodiments, the lab worker may put the biological sample into a container which will be introduced into the screening room. In a particular but non-limiting example, the container is a glass container with one or more small openings which allow for a detection animal to detect the scent inside the container. In particular embodiments, preparing the biological sample may be automated using robotics and other machines. In particular embodiments, preparing the biological sample comprises attaching a container containing the biological sample to an olfactometer system. In particular embodiments, the method of receiving the biological sample and preparing the biological sample occurs in a sterile environment.

The method 100 may then continue at step 108 with a person or machine placing the biological sample into the testing system. In one embodiment, the testing system is an olfactometer system, wherein the samples are placed into a receptacle of an olfactometer system, wherein the olfactometer system comprises a plurality of receptacles, and wherein each receptacle is connected to a sniffing port. In one embodiment, the receptacles and the sniffing port are connected, but the receptacles and the sniffing port are in separate rooms. The structure of the olfactometer system is discussed herein. The structure of an example screening room and testing facility is discussed herein. The screening room contains a plurality of sniffing port. In one embodiment, a biological sample is placed in a receptacle of the sniffing port. In a particular embodiment, the sniffing ports are connected to an olfactometer system. In a particular embodiment, the sniffing port is connected to a receptacle, which is operable to hold a biological sample. The screening room is configured to hold the biological samples of a plurality of users. In particular embodiments, each receptacle contains the biological sample of a different user.

The method 100 may then continue at step 110 with a person or a machine bringing in one or more detection animals to analyze the biological samples in the screening room. In particular embodiments, a detection animal enters the screening room to sniff each sniffing port. The animal may enter with a handler (e.g., to guide the animal to the biological samples) or without a handler. In particular embodiments, the detection animal walks around the screening room (with or without a handler) to sniff each sniffing port to detect one or more target odors. In particular embodiments, the detection animal goes to each sniffing port and sniffs each sniffing port to detect one or more target odors. In particular embodiments, the detection animal will perform a run, wherein a run comprises sniffing each sniffing port in the screening room. In particular embodiments, the detection animal will perform several runs. In particular embodiments, biological samples are transferred to a different sniffing port in the screening room in between runs and the detection animal is brought in after the samples are transferred to perform another run.

In particular embodiments, if the detection animal provides the same results in two different runs, then the system will determine the result to be valid, and will instruct a person or machine to bring a second detection animal to the screening room to perform a run. In particular embodiments, if the detection animal provides different results in two or more runs, the detection animal will repeat the process of sniffing each sniffing port until a consistent result is established, or until the detection animal has reached a maximum number of allowed runs per session. Although this disclosure describes a particular protocol for a run, this disclosure contemplates any suitable protocol for a run. The detection animal may be any suitable non-human animal with olfactory senses, such as a canine. Although this disclosure describes analyzing biological samples with particular types of detection animals, this disclosure contemplated analyzing biological samples with any suitable type of detection animal. As an example and not by way of limitation, other suitable types of detection animals may include grasshoppers, ants, bears, and rodents, such as rats and mice. In particular embodiments, upon the positive identification of a target odor, the detection animal may be provided with a reward by either a human or a machine executing an automated reward mechanism. In particular embodiments, the reward may be one or more of: a food, a toy, or positive feedback from a human or machine. In particular embodiments, an additional detection animal will be brought into the screening room to sniff the sniffing port to detect a particular target odor. In particular embodiments, one or more different detection animals will be brought into the screening room, one after the other, to detect for target odor(s) in each sniffing port. In particular embodiments, five detection animals may be used to analyze a particular set of samples in the screening room. In particular embodiments, the decision of whether a particular sniffing port contains a target odor is made by analyzing signals generated from all canines in a particular test session. In particular embodiments, the process of operating and monitoring the test procedure may be automated.

In particular embodiments, a canine may indicate a particular sample to contain the target odor by performing a trained action. In particular embodiments, the trained action may comprise a body pose. A body pose may include, but is not limited to, standing next to the sniffing port, sitting next to the sniffing port, looking at a handler, or lying next to the sniffing port. In particular embodiments, the trained action may comprise an act, such as emitting a sound. In particular embodiments, after a detection animal indicates a particular sample to contain the target odor, that particular sample will be removed from the screening room and the detection animal will perform one or more additional runs to detect target odors in the remaining samples. Although this disclosure describes detection animals performing a trained action in a particular manner upon detection of a target odor, this disclosure contemplates any suitable trained action upon detection of a target odor.

In particular embodiments, detection animals are selected based on one or more of their natural abilities which include: odor detection abilities, strength, natural instincts, desire to please humans, motivation to perform certain actions, sharpness, tendency to be distracted, or stamina. In particular embodiments, detection animals are trained through operant conditioning, which encompasses associating positive behavior with a reward, negative behavior with a punishment, or a combination thereof. In particular embodiments, detection animals are trained using only a reward-based system. In particular embodiments, detection animals are taught to sit when they detect a target odor. In particular embodiments, detection animals may be taught to identify a plurality of target odors and exhibit a particular behavioral, physiological, or neurological response upon identification of a particular target odor. As an example and not by way of limitation, the target odor is a cancer VOC profile. In particular embodiments, a trainer may teach a detection animal to associate a target scent with a reward. In particular embodiments, an animal may be trained on odors through a sample which contains a mixture of various odors. In particular embodiments, a trainer may present odors separately but train animals on odors at the same time (intermixed training). In particular embodiments, the detection animal may be trained to exhibit a different response for different stages of cancers or different types of cancers. Although this disclosure describes training detection animals in a particular manner, this disclosure contemplates describes training detection animals in any suitable manner.

In particular embodiments, detection animals undergo a multi-level training program. As an example and not by way of limitation, detection animals may undergo a three-level training program which may comprise a first-level training program for preparing the detection animal, a second-level training program for developing abilities of outcomes detection, and a third-level training program for developing assimilation of sniffing abilities and simulation of real situations. In particular embodiments, the first-level training program comprises one or more of: leash training, basic discipline training, socialization (e.g. exposure to external stimulations during work wherein the stimulation includes one or more of other animals, cars, or people), or training basic scanning technique. In particular embodiments, the second-level training program comprises one or more of: assimilation of the outcome scent (e.g. combining food into the training), assimilation of the outcome scent (e.g. weaning from food combination), advanced discipline training, exposure to various distractions and outcomes, or increasing scan volumes and sniffing quality. In particular embodiments, the third-level training program comprises one or more of: assimilation of various cancer scents, combination(s) of different scents for detection, assimilation of various outcome scents and concentrations, combination(s) of different scents for detection, exposure to complex outcomes, or simulations of real-life situations. The training may be done in a double-blind manner, such that neither the handler nor persons handling training samples know whether test samples are positive or not during the training. In particular embodiments, the detection animals may pass a first level of training before moving onto the next level of training. Although this disclosure describes training detection animals in a particular manner, this disclosure contemplates describes training detection animals in any suitable manner.

In particular embodiments, detection animals are not trained to exhibit specific behavioral responses in response to specific biological samples. In particular embodiments, a detection animal (e.g., a canine) will have specific responses (e.g., a neurological response) to particular odors. In particular embodiments, the neurological response comprises data from an EEG. In particular embodiments, a ML-based neurological model may be trained on correlations between a detection animal's neurological response and a target odor.

The method 100 may then continue at step 112 with a one or more of sensors collecting data in real-time from the screening room and from the detection animal. In particular embodiments, the one or more sensors comprise one or more behavioral sensors, one or more physiological sensors, one or more neurological sensors, one or environmental sensors, and one or more operational sensors.

As an example and not by way of limitation, behavioral sensors may comprise one or more of: cameras, audio recorders, accelerometers, thermal sensors, or distance sensors which monitor the behavior of the detection animals as the animals detect for scents in the sniffing ports. In particular embodiments, videorecorders and/or cameras may transmit images of the detection animals and data containing timestamps of the images, which may enable calculations including a duration of a sniff. A duration of a sniff is the time the detection animal spends sniffing a particular sample. In particular embodiments, the cameras may transmit frames from a plurality of angles, and the frames are analyzed to extract measurements such as a duration of a sniff or a time a detection animal spent at a sniffing port. In particular embodiments, image data (e.g., from a camera/video record) comprises a sitting detection outcome (e.g., an indication of whether a detection animal sits down after being exposed to a biological sample). Using the sitting detection outcome, the disease-detection system can also measure the sitting duration and a time between sniffing to sitting, which may be input into a ML-model. In particular embodiments, the disease-detection system calculates the amount of time between a sniff and the moment the animal signals it found a target odor. In particular embodiments, audio sensors transmit the sounds of the sniffs, which may include the duration and intensity of a particular sniff. In particular embodiment, a behavioral sensor may be worn by a detection animal. As an example and not by way of limitation, a behavioral sensor may comprise one or more of: accelerometer, a gyroscope, or a camera. In particular embodiments, the behavioral sensor provides information about the animal's movements and behavior in the screening room. In particular embodiments, a distance sensor (e.g., an ultrasonic sensor, an infrared sensor, a LIDAR sensor, or a time-of-flight distance sensor) may detect the behavior of an animal, including when the duration that the detection animal's head is in or near the sniffing port. Although this disclosure describes sensors in a particular manner, this disclosure contemplates any suitable sensors measuring any suitable measurements.

As an example and not by way of limitation, physiological sensors may comprise one or more of a: heart rate monitor, heart rate variability monitor, temperature sensor, galvanic skin response (GSR) sensor, or a breath rate sensor. In particular embodiments, the physiological sensor may be worn by the detection animal. In particular embodiments, the physiological sensor is not worn by the detection animal. Although this disclosure describes sensors in a particular manner, this disclosure contemplates any suitable sensors measuring any suitable measurements.

As an example and not by way of limitation, neurological sensors may comprise one or more of sensors operable to gather: Electroencephalogram (EEG), Functional Near Infrared Spectroscopy (fNIR), Magnetic Resonance Imaging (MRI), or Functional Magnetic Resonance Imaging (fMRI). As an example and not by way of limitation, the sensor may comprise an EEG cap worn on the head of a detection animal to monitor the animal's neurological signals. Although this disclosure describes sensors in a particular manner, this disclosure contemplates any suitable sensors measuring any suitable measurements.

As an example and not by way of limitation, environmental sensors may comprise one or more of: temperature sensors, humidity sensors, noise sensors, and air sensors. In particular embodiments, environmental sensors may measure air particulate levels or air filtration levels, including air pollution levels and the rate of air exchange in the screening room. In particular embodiments, environmental sensors may include noise sensors which measure the noise level of the screening room. In particular embodiments, environmental sensors may comprise one or more gas sensors, including a chemical or electrical sensor that can measure a total amount of VOCs or detect the presence of a particular VOC. In particular embodiments, the gas sensor can detect a quality or quantity of an inorganic gas (such as one or more of $CO_2$, CO, $N_2$, or $O_2$), wherein the inorganic gas is correlated to a quality or quantity of a biological sample. In particular embodiments, sensors are placed at receptacles which contain biological samples to collect measurements at the receptacles. Example sensors include: a gas sensor to measure a VOC quality or quantity, an audio sensor to measure one or more auditory features (e.g., a sound, duration, or intensity of a sniff), an infrared sensor to measure a duration of a sniff, or a pressure sensor to measure a pressure of the detection animal's nose against a sniffing port. Although this disclosure describes sensors in a particular manner, this disclosure contemplates any suitable sensors measuring any suitable measurements.

As an example and not by way of limitation, operational sensors may comprise one or more of: sensors in an olfactometer system, sensors for animal management (e.g., a RFID card which identifies a particular canine), and sensors for sample management (e.g., a QR code scanner which scans a unique QR code associated with each biological sample). In particular embodiments, step 112 comprises real-time monitoring and analysis, described herein. In particular embodiments, Step 112 comprises managing operational data received from the operational sensors described herein, including data corresponding to sensor performance, sample tracking, and detection animal tracking. Although this disclosure describes sensors in a particular manner, this disclosure contemplates any suitable sensors measuring any suitable measurements.

The method 100 may then continue at step 114 with processing and transmitting certain data obtained from the various sensors to one or more ML-models. In particular embodiments, the disease-detection system collects data from a plurality of sensors comprising one or more of behavioral, physiological, and neurological sensors. In particular embodiments, the sensors measure one or more of: animal behavior, animal physiological patterns, or animal neurological patterns. In particular embodiments, processing data comprises synchronizing data, ensuring data security, transforming raw data into a refined data which is input into one or more ML-models, managing laboratory resources, and performing test and training analytics.

At step 116, one or more ML-models analyzes one or more signals from the sensor data to determine one or more biological conditions and a confidence score. As an example and not by way of limitation, the one or more ML-models comprise one or more of: one or more ML-models for a particular detection animal (e.g., a dog-specific ML-model), one or more ML-model for a plurality of detection animals (e.g., a dog pack-specific ML-model, also referred to herein as a "lab-result ML-model"), one or more test stage-specific models (e.g., a ML-model for stage 1 of a test), one or more ML-models trained on disease states (e.g. a positive or negative determination of cancer), one or more ML-models trained on cancer types (e.g., breast cancer, lung cancer, colon cancer, prostate cancer), one or more ML-models trained on cancer stages (e.g., stage 1, stage 2, stage 3, or stage 4), one or more neurological-based ML-models, or one or more monitoring ML-models (e.g., monitoring the behavioral drift of a detection animal). In particular embodiments, an ML-model may be configured to detect a particular stage or type of cancer (e.g., cancer at stage 2, a breast cancer at stage 2, a breast cancer, etc.). In particular embodiments, the ML-model is operable to perform a monitoring or a predictive function. Although this disclosure describes ML-models in a particular manner, this disclosure contemplates any suitable ML-model for disease detection.

In particular embodiments, the confidence score is calculated based on a probability of the disease state. In particular embodiments, the confidence score is calculated based on a probability of the disease state and a confidence prediction interval. In particular embodiments, the one or more ML-models predict a disease state and likelihood value(s) of the disease state(s) by amplifying and analyzing one or more of: animal behavior (such as a duration of a sniff, a body pose, etc.), physiological patterns, and neurological signals, or inputted patient data. Inputted patient data includes one or more of: family medical history, patient medical history (including lifestyle), patient age, patient gender, or patient demographical data.

In particular embodiments, the ML-based disease-detection model is trained on a dataset of target odors and detection events. As an example and not by way of limitation, detection events may include one or more of signals relating to: animal behavior, physiological signals, or neurological signals. In particular embodiments, the biological condition may be one or more of: a cancer (e.g., breast cancer, lung cancer, prostate cancer, or colorectal cancer), *Helicobacter pylori* (*H. pylori*) infection, inflammatory bowel disease, or Crohn's disease. In particular embodiments, the biological condition may also include a particular stage of cancer or a particular type of cancer.

The method 100 may then continue at step 118 with the disease-detection system informing the user or the user's doctor of one or more biological conditions and a confidence score associated with each condition.

Particular embodiments may repeat one or more steps of the method of FIG. 1, where appropriate. Although this disclosure describes and illustrates particular steps of the method of FIG. 1 as occurring in a particular order, this disclosure contemplates any suitable steps of the method of FIG. 1 occurring in any suitable order. Moreover, although this disclosure describes and illustrates an example method for ML-based disease-detection of behavioral, physiological and neurological patterns of detection animals including the particular steps of the method of FIG. 1, this disclosure contemplates any suitable method for ML-based disease-detection by monitoring and analyzing behavioral, physiological and neurological patterns of detection animals including any suitable steps, which may include all, some, or none of the steps of the method of FIG. 1, where appropriate. Furthermore, the ML algorithms and functions of the ML-models described herein may include deep learning algorithms, supervised learning algorithms, or unsupervised learning algorithms.

Figure 2:
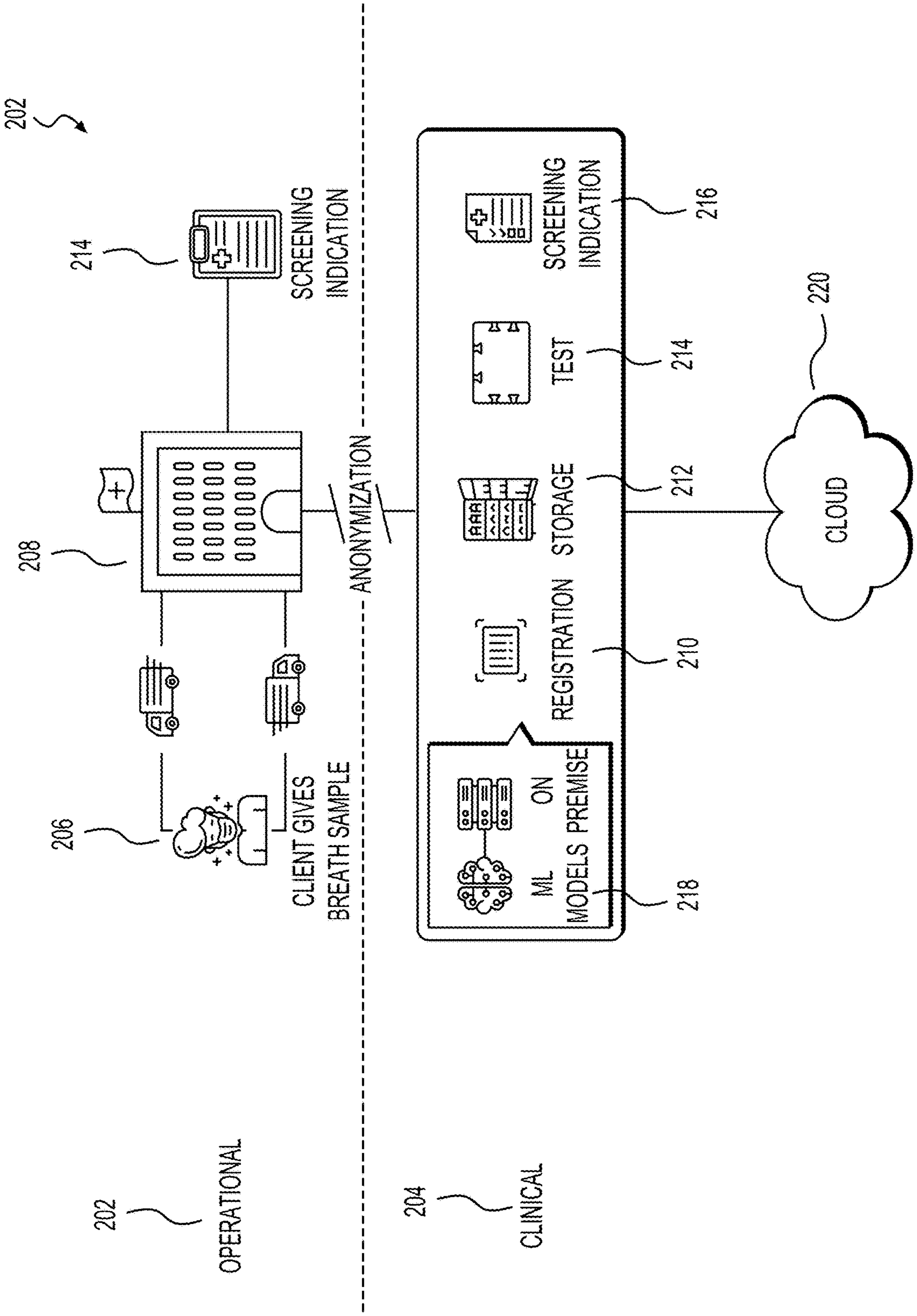
FIG. 2 illustrates an example disease-detection method.

FIG. 2 depicts a disease-detection system which comprises an operational component 202 and a clinical component 204. The operational and clinical components are strictly separated, and all medical records stored on the system are anonymized, encrypted, and do not allow for client identification.

The operational component 202 handles the patient-facing workflow, including the logistics, activation, and authentication of sample kits, test instruction and guidance, and sample management. For example, the operational component comprises obtaining a breath sample from a client 206. In particular embodiments, the breath sample is collected by a medical professional, who then documents the sample collection into a database. The database, which further comprises medical information of the patient, is sent to the clinical facility. Further, the breath sample is sent to a clinical or laboratory facility 208 for testing. The operational component provides a wide range of filtering and sorting capabilities which allow the lab team to retrieve and monitor each and every sample.

The clinical component 204 handles the clinical workflow including: sample registration 210 and management, sample storage 212, sample testing 214, and providing a screening indication 216. Upon arrival of the sample, the sample is recorded and stored. In particular embodiments, samples may be stored at room temperature for up to one year. Although this disclosure describes storing samples in a particular manner, this disclosure contemplates storing samples in any suitable type of manner.

The testing is performed using ML-models 218, which receives data from behavioral sensors, environmental sensors, physiological sensors, neurological sensors, as well as patient data. The clinical component 204 aggregates data in a robust database and supports complex and flexible reporting systems. The data is streamed and processed, and different databases comprising raw data, target odors, and detection events are stored locally in the lab's server, as well as on the cloud 220.

Moreover, although this disclosure describes and illustrates an example method for a disease-detection system including the particular system of FIG. 2, this disclosure contemplates any suitable method for a disease-detection system including any suitable steps, which may include all, some, or none of the system components of FIG. 2.

User Experience

Figure 3:
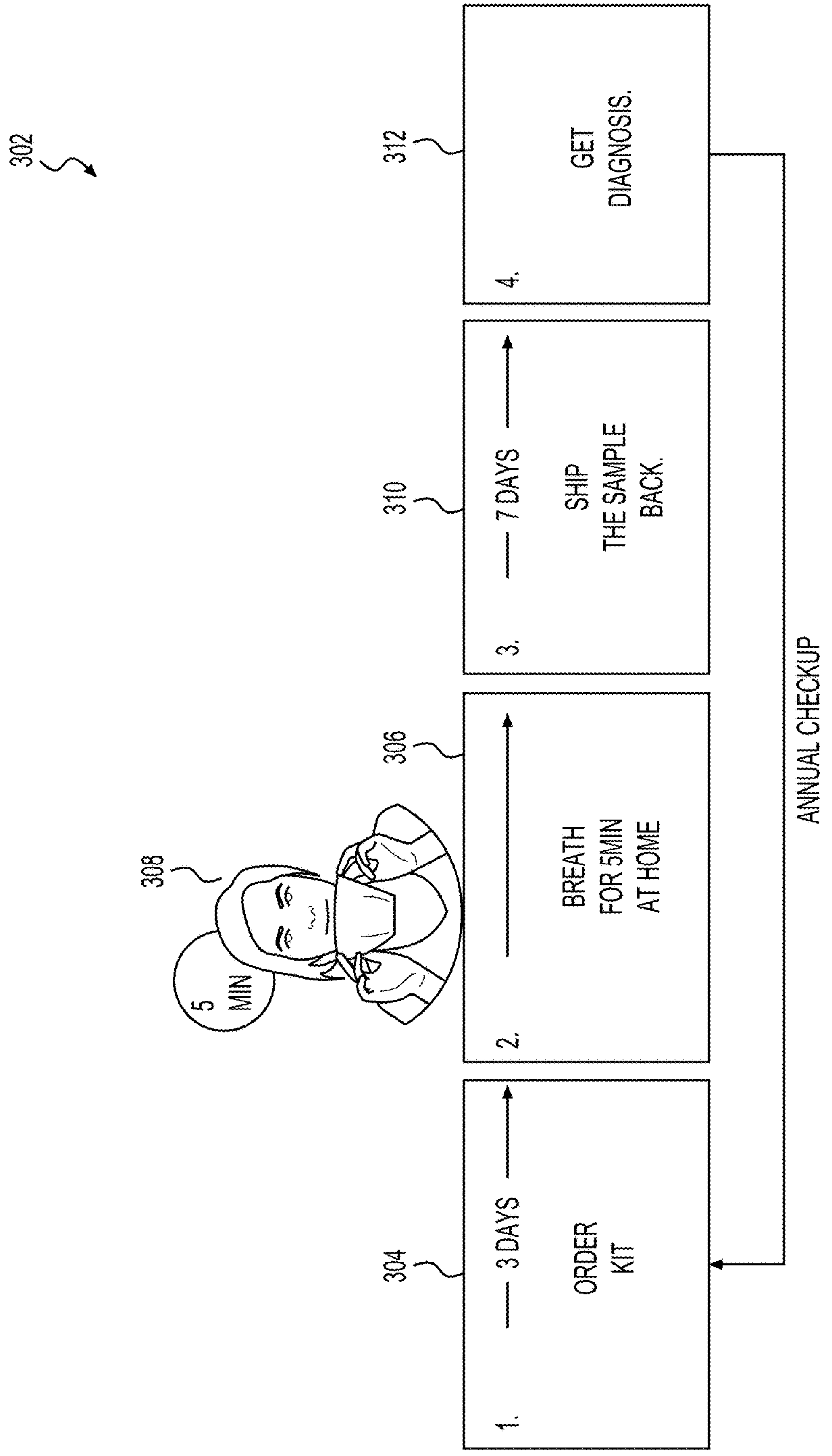
FIG. 3 illustrates an example disease-detection method.

FIG. 3 illustrates a flow diagram of an example method of screening and diagnostics from the user perspective. The method 302 may begin at step 304 with a user (e.g., a patient) or a physician ordering a test. In particular embodiments, a high-risk patient (e.g., one that is at a high risk for breast cancer) may be identified by a physician or by a database comprising patient data. In particular embodiments, a patient may be identified as high-risk after completing a questionnaire about their family medical history and personal medical history.

In particular embodiments, the user receives a sample collection kit which contains a collection device. The sample collection kit will be discussed herein. In a particular embodiment but non-limiting embodiment, the collection device is a facial mask which the user may breathe into. Next, at step 306, the user 308 breathes into the facial mask. In an example embodiment, the user 308 breathes into the facial mask for five minutes. In particular embodiments, the user may perform some other biological function to enable the user's biological sample to be placed into the collection device. For example, the user may swab their mouth and place the swab into a collection device. As another example, the user may collect their urine in a collection device. Next, at step 310, the user packs the biological sample into company-provided packaging and ships the sample to the test facility. Next, at step 312, the user receives the results, which may include a diagnosis. In particular embodiments, the diagnosis includes an identification of one or more biological conditions and a confidence score of each biological condition. FIGS. 5-6 depict non-limiting examples of a sample collection device. For example, the collection device may be a tube, a cup, or a bag, or any suitable collection kit which may be used to collect a biological sample. In particular embodiments, the biological sample may be one or more of: breath, saliva, urine, feces, skin emanations, stool, biopsy, or blood. Although this disclosure describes biological samples in a particular manner, this disclosure contemplates biological samples in any suitable manner.

Sample Collection Protocol

Figure 4:
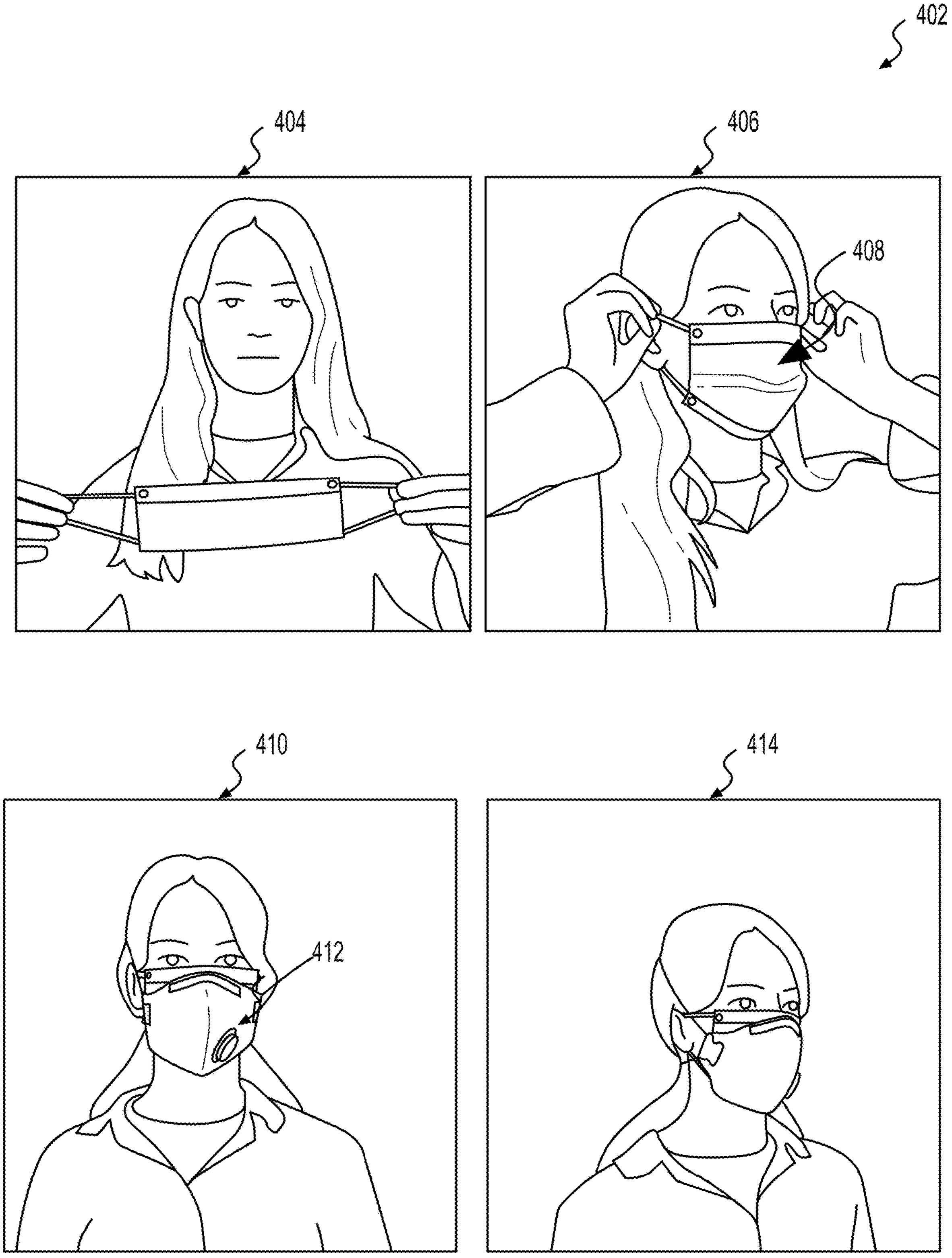
FIG. 4 illustrates an example disease-detection method.

FIG. 4 depicts an example sample collection protocol. Samples may be collected at a patient's home or in a medical facility. An example collection protocol 402 is described below. Although this disclosure describes an example protocol for obtaining a biological sample, this disclosure contemplates any suitable method for obtaining a biological sample.

Patients are instructed to not smoke for at least two hours before breath collection. Patients are instructed to not consume coffee, alcohol, or food for at least an hour before breath collection. The patient is instructed to breath only through the mouth, and not through the nose. First, at step 404, the patient performs a "lung wash" step wherein the patient breaths in a normal, relaxed manner for one minute. Next, the patient is instructed to take a full breath so that the full volume of the lungs is filled, and then to hold the breath for at least five seconds. Then, at step 406, the patient puts on a first mask 408 (e.g. the "sample collection mask"). Next, at step 410, the patient puts on a second mask 412 (e.g. the "isolation mask") over the first mask. The purpose of the second mask is to filter the incoming air from the environment that the patient inhales. In particular embodiments, the second mask may be placed over the first mask such that a predetermined gap is formed between the first mask and the second mask. The purpose of this space between the first mask and the second mask is to increase the VOC absorbance by the first mask. For instance, the first mask (e.g. the sample collection mask) has a first portion which faces the patient and a second portion which faces away from the patient. In particular embodiments, the first mask may fit snugly against a patient's mouth and nose. As a person exhales, the exhaled air is first passed through the first portion of the first mask, and the first portion collects the breath and aerosols exhaled by a patient. Then, the second portion of the first mask, which is in the predetermined gap formed between the first mask and the second mask, is operable to passively absorb the breath and aerosols exhaled by the patient.

The sample collection mask and the isolation mask are described in further detail herein. In a particular embodiment, the patient holds their breath for a minute, the protocol continues at step 414, wherein the patient should breathe normally, only through their mouth, for at least three minutes. A benefit of this example of this example breathing and collection protocol is to maximize the collection of alveolar breath from the patient. Alveolar breath is breath from the deepest part of the lung.

The first mask and the second mask should cover the patient's nose and mouth. Further, there may be minimal gaps between the mask and the patient's face, to allow for all inhaled and exhaled air to go through the mask. Additionally, patients should not talk during the sample collection procedure while they are wearing the sample collection component. After the patient has breathed through their mouth for five minutes, while wearing both the first mask and the second mask, the second mask is carefully removed. Then, the first mask is removed. In particular embodiments, the first mask is removed using sterile gloves, and the mask is folded in half by touching only the outer layer of the mask. Next, the mask is inserted into a storage component, e.g. a bag or a container, sealed, and then transported to a laboratory facility. In particular embodiments, the second mask (e.g. the isolation mask) is discarded.

Although this disclosure describes and illustrates an example method for sample collection including the particular steps of the method of FIG. 4, this disclosure contemplates any suitable method for sample collection including any suitable steps, which may include all, some, or none of the steps of the method of FIG. 4.

Sample Collection Kit

In particular embodiments, the sample collection kit contains a collection device which collects a biological sample that could be one or more of breath, saliva, sweat, urine, other suitable types of samples, or any combination thereof. The samples may contain VOCs or aerosols, which may be detectable by a detection animal. Starting an early stage in the development of cancerous tumors, VOCs are released from the cells to their microenvironment and to the circulation system. From the circulation system, VOCs can be further secreted through other bio-fluids such as through aerosols, gases, and liquid droplets from the respiratory system. Each type and stage of cancer has a unique odor signature created from the either different or the same VOCs in different combinations and proportions. By breathing into the collection kit over several minutes, VOC biomarkers originating from all around the body may be captured with high sensitivity. Although this disclosure describes biological samples in a particular manner, this disclosure contemplates biological samples in any suitable manner.

Figure 5B:
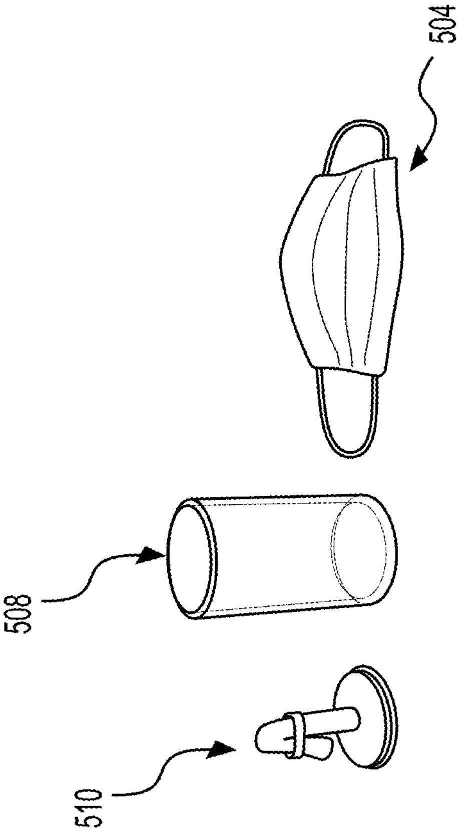
FIGS. 5A-5B illustrate an example collection kit.
Figure 5A:
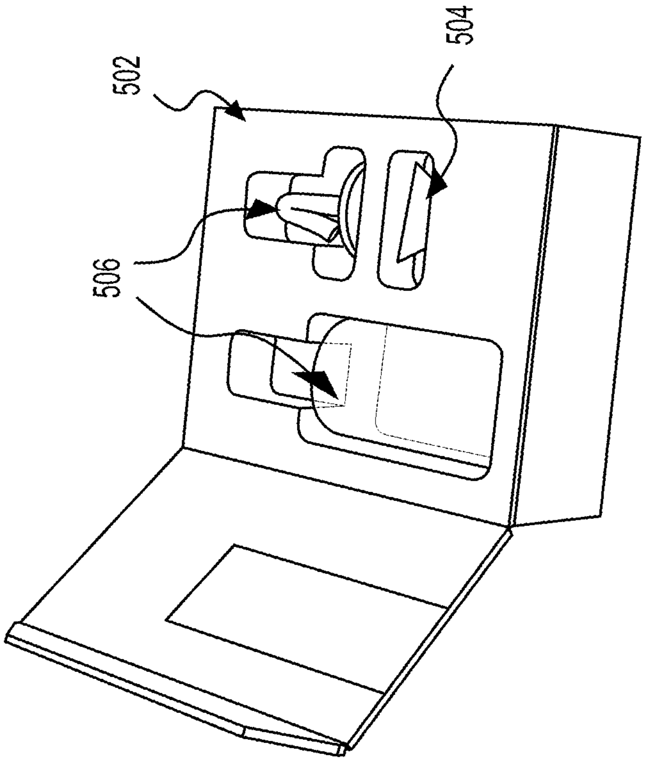

FIGS. 5A-5B illustrate an example sample collection kit. FIG. 5A depicts a sample collection kit comprising a box 502 which houses a sample collection component 504 (e.g., a mask) and a storage component 506. FIG. 5B depicts an example sample collection component 504 and storage component 506 removed from the box.

Sample Collection Component

The sample collection component is operable to absorb aerosols and droplets which contain VOCs into the sample collection component. Further, the sample collection component is operable to adsorb gaseous molecules (e.g., VOCs) onto the surface of the sample collection component. In particular embodiments, the sample collection component is formed of a plurality of layers, wherein each layer is made of polypropylene. For example, the sample collection component may be an off-the-shelf 5-layer polypropylene mask. For instance, the off-the-shelf mask may be an N-95 or a KN-95 mask. In particular embodiments, the polypropylene absorbs aerosols and liquid droplets from the patient. In particular embodiments, the sample collection component has a filtering efficiency of 95% for particles of 0.3 micron or more. In particular embodiments, the sample collection component may also comprise an active carbon layer which is operable to adsorb VOCs. In other embodiments, the sample collection component comprises two layers of polypropylene and one layer of active carbon. Based on the above descriptions, including at least the desired filtration level and the desired absorptive and adsorptive properties, this disclosure contemplates using any materials which may be suitable to achieve the desired function of the sample collection component.

Isolation Component

The isolation component is operable to provide a barrier between the environment and the sample collection component, to enable the patient to inhale clean air. For example, the isolation component protects the sample collection layer from contamination by the external environment; the contamination may be from ambient pollution or external VOCs/aerosols from someone other than the patient. In particular embodiments, the isolation component is made of polypropylene. In other embodiments, the isolation component may be formed of cotton. In particular embodiments, the isolation component further comprises an active carbon layer for improved filtering. In particular embodiments, the isolation component is rigid such that when the patient wears the isolation component over the sample collection component, there is a gap between the sample collection component and the isolation component. In particular embodiments, this gap maintains space for breath to accumulate in the gap such that additional VOCs may be collected by the sample collection component. For example, the gap increases the amount of gaseous VOCs adsorbed on the outer surface of the sample collection component. In particular embodiments, the isolation component creates a greater volume over the patient's mouth and nose than the sample collection component.

In particular embodiments, the sample collection component and the isolation component are combined into one device.

Based on the above descriptions, including at least the desired filtration level and the desired rigidity or space-maintaining capabilities, this disclosure contemplates any other materials which may be suitable to achieve the desired function of the isolation component.

Storage Component

The storage component is operable to maintain a barrier between the collected biological sample and the external environment, and maintains sterility through at least the receipt of the biological sample by the testing facility. In particular embodiments, the storage component prevents the biological sample (e.g., the exhalant) from being exposed to environmental contamination during transport. In particular embodiments, the storage component prevents the biological sample from leaking or from being diluted. In particular embodiments, the storage component is resealable. In particular embodiments, the storage component is heat-resistant. In particular embodiments, the storage component has a minimal scent signature.

FIG. 5B depicts an example storage component 506 and a sample collection component 504. In particular embodiments, the storage component 506 may comprise a receptacle 508 and a cap 510, wherein the cap further comprises a seal.

Figure 6B:
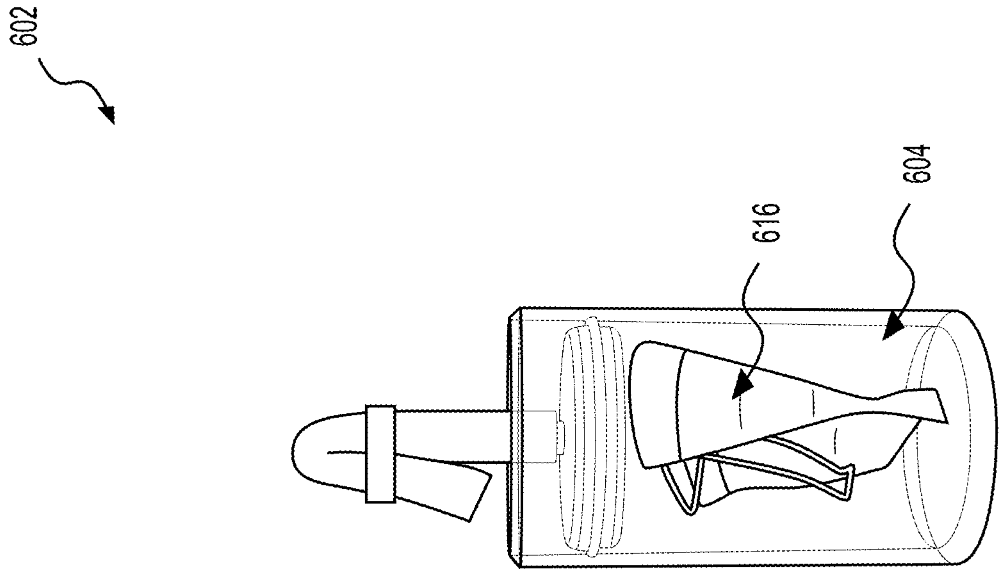
FIGS. 6A-6B illustrate an example collection kit.
Figure 6A:
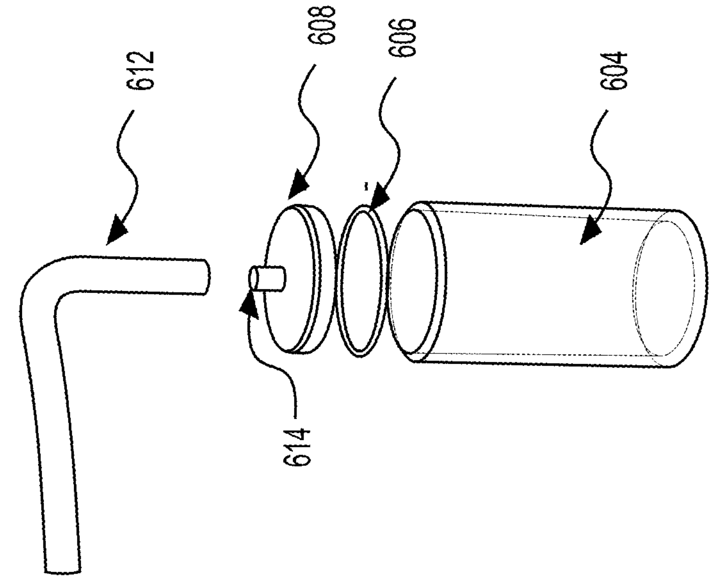

FIGS. 6A and 6B depict another view of an example storage component 602. FIG. 6A depicts an unassembled view of the storage component 602 and FIG. 6B depicts an assembled view of the storage component 602. In particular embodiments, the storage component comprises a receptacle 604, a gasket 606 which goes around the edge of a cap 608, and a tube 612 connected to the cap 608. In particular embodiments, the storage component has minimal gas permeability. In particular embodiments, the receptacle 604 and cap 608 are made of a rigid, inert material, such as stainless steel, glass, or silicone. In particular embodiments, the storage component is sealed with a gasket 606 formed of polytetrafluoroethylene (PTFE) and a cap 608, wherein the cap comprises a flat portion and a jutted portion 614 having a circumference less than that of the flat portion. In particular embodiments, the tube 612 is flexible and formed of PTFE.

In particular embodiments, the storage component is made of Mylar. In particular embodiments, the storage component may be a scalable bag. Although this disclosure describes storage components in a particular manner, this disclosure contemplates storage components in any suitable manner.

In particular embodiments, after the biological sample has been collected in the sample collection component 616, the sample collection component 616 is placed into receptacle 604 and sealed with a cap 608, wherein gasket 606 is located around the circumference of cap 608. In particular embodiments, the cap 608 has a flat portion and a jutted portion 614, wherein the jutted portion has a circumference less than that of the flat proton. In a particular embodiment, the gasket 606 around the cap 608 is operable to keep the sample collection component 616 sealed from the external environment. In particular embodiments, a clinician or the patient can push the cap into the receptacle 604. In particular embodiments, the cap can be only pushed into the receptacle for a set distance due to the interior pressure in the receptacle 604 from the compressed air. In particular embodiments, the receptacle 604 comprises an internal protrusion which functions as a mechanical stop for the cap.

The sample collection kit may also contain an isolation component (not pictured). In particular embodiments, the sample collection component 616 may be a mask that fits tight over the patient's mouth and nose to capture as much exhalant as possible. The exhalant may comprise one or more of liquids, gases, or aerosols from the patient's breath. For example, the majority of the exhalant from the patient may pass through the sample collection component.

In particular embodiments, the collection kit may incorporate a method of user authentication. In particular embodiments, the collection kit may be designed to preserve odors for a long period of time. In particular embodiments, the collection kit will assist the user in removing background odors. In particular embodiments, the collection kit will indicate to a user when an appropriate amount of biological sample has been collected or authenticate that the user successfully provided a biological sample. In particular embodiments, the user places the collection device containing the biological sample into a hermetically sealed container which preserves the integrity of the biological sample. In particular embodiments, the user seals the sample into a bag, packs it up in a box or envelope, and sends the box or envelope to a testing facility.

Laboratory Facility

Figure 7:
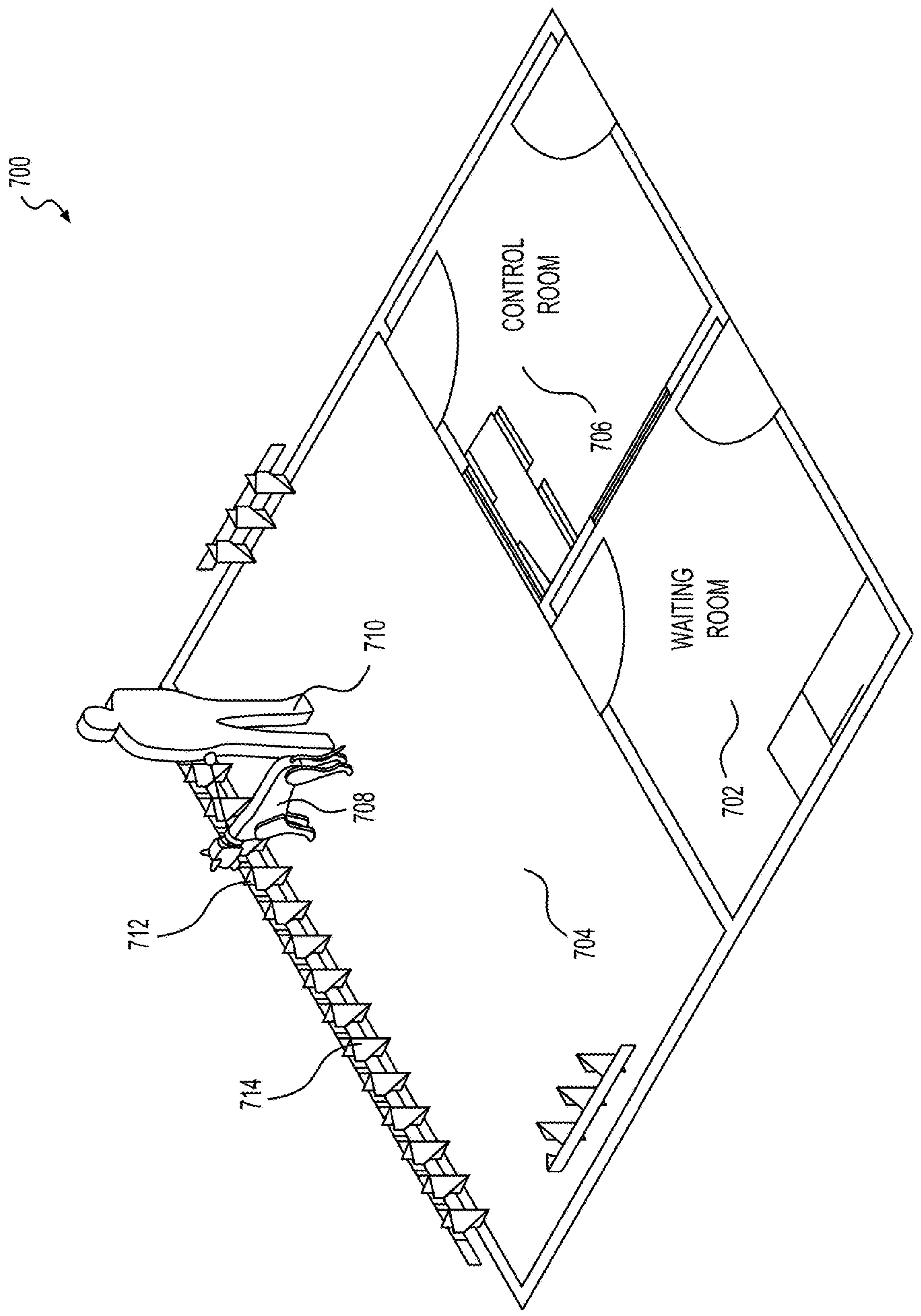
FIG. 7 illustrates an example test facility.

FIG. 7 illustrates an example laboratory facility 700. In particular embodiments, the laboratory facility 700 comprises a plurality of rooms: a waiting room 702, a screening room 704, and a control room 706. In particular embodiments, sensors are placed throughout the laboratory facility 700, and in particular, in screening room 704 to monitor conditions of the screening room and behaviors, physiological conditions, and neurological conditions of one or more detection animals in the screening room. In particular embodiments, the waiting room 702 is used for detection animals, and optionally, a human handler 710, to wait until they are allowed in the screening room 704. In particular embodiments, the disease-detection system analyzes one or more of: behavior, physiological conditions, or neurological conditions of the detection animal to ensure the detection animal is ready for use in the screening room 704.

In particular embodiments, the screening room 704 contains one or more receptacles, including receptacles 712 and 714. Each receptacle may contain a biological sample. In particular embodiments, the detection animal, optionally a canine 708, sniffs each receptacle. In particular embodiments, a separate screening room (not pictured) may be used for particular test(s), such as tests to collect neurological data. As an example and not by way of limitation, neurological data (e.g., EEG data) may be collected in a different screening room from the screening room 704 depicted in FIG. 7. In particular embodiments, the biological samples(s) for testing are not placed directed in the screening room 704; instead, the samples are placed in an olfactometer system connected to the screening room 704. In particular embodiments, a sniffing port of the screening room 704 is connected via one or more flow paths to an olfactometer system in a separate room which houses the biological samples during testing. In particular embodiments, when the canine identifies a target odor in a receptacle, the canine sits next to the receptacle. In particular embodiments, an automated reward mechanism is located at or near the receptacle. In particular embodiments, the automated reward mechanism will provide a reward to the detection animal in accordance with a proprietary reward policy and will reward the animal based on its performance. As an example and not by way of limitation, the reward may be a food item.

In particular embodiments, the control room 706 contains a window which allows a person or machine to view the screening room 704. In particular embodiments, one or more lab workers may be present in the control room 706 and monitor the screening procedure to ensure the screening is performed according to standard procedures. In particular embodiments, one or more persons in the control room ensures that samples are placed in the correct receptacles in the screening room 704.

In particular embodiments, a laboratory facility may contain ten screening rooms and be able to facilitate 600 screenings per hour and 1.2 million screenings per year. In particular embodiments, twenty canines are utilized in a laboratory facility. In particular embodiments, one test may be verified by four canines. Although this disclosure describes and illustrates a particular laboratory facility having particular components in a particular arrangement, this disclosure contemplate a laboratory facility have any suitable components in any suitable arrangement.

Olfactometer System

Figure 8:
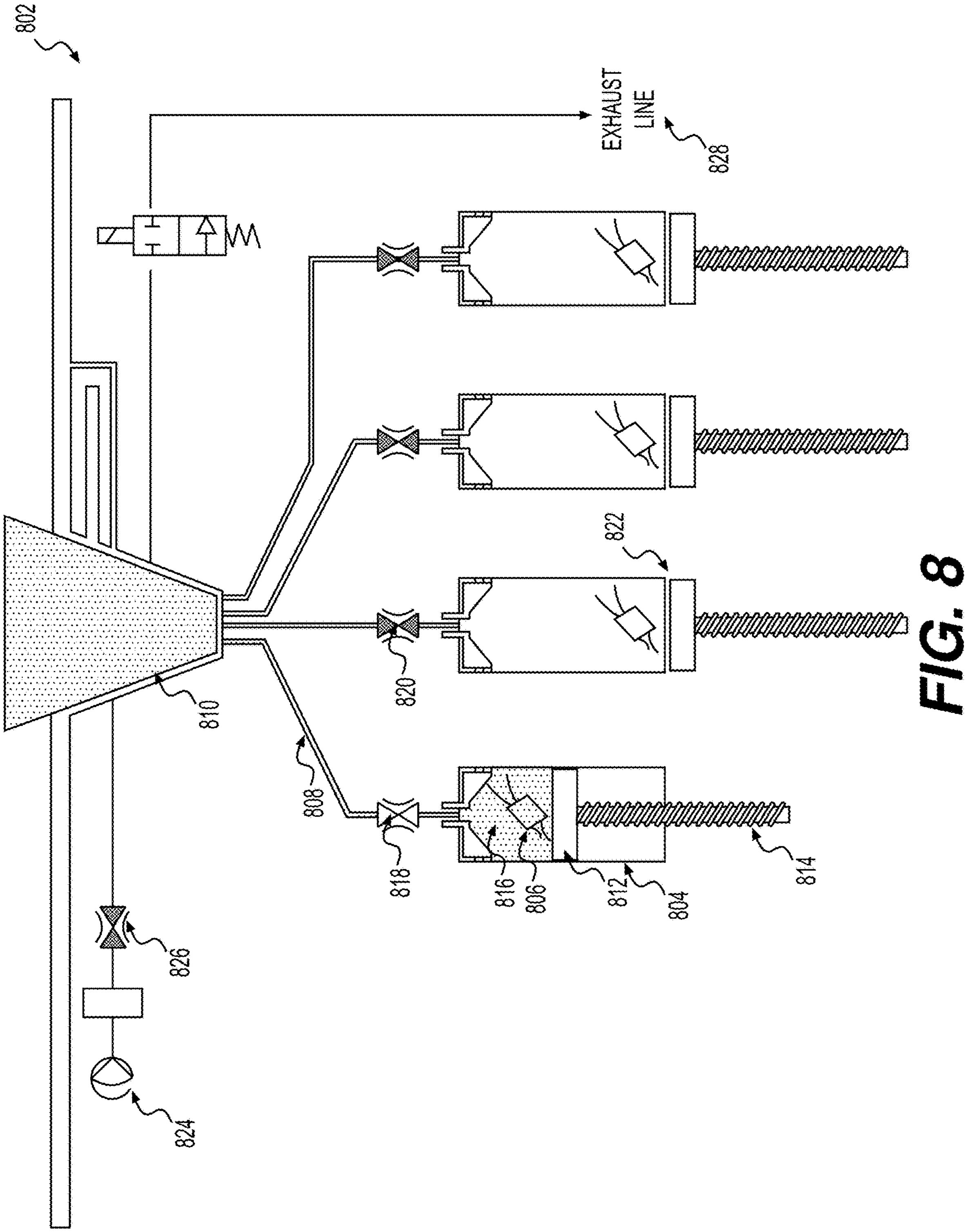
FIG. 8 illustrates an example odor detection system.

FIG. 8 illustrates an example olfactometer system 802. The olfactometer system comprises a plurality of receptacles 804. Each receptacle 804 is operable to hold a biological sample 806. The biological sample 806 may optionally be a mask. Further, a flow path 808 connects each receptacle to sniffing port 810. Each receptacle has a corresponding piston 812 and a piston driving portion 814 which can press the air controllably out of receptacle 804, thus transporting the odor-soaked air 816 from biological sample 806 to the sniffing port 810 via the flow path with zero dilution and in a measurable, repeated, and computed way. The piston driving portion 814 is coupled to a controller which determines the movement the piston will undergo. For example, the olfactometer delivered a measured amount of odor-soaked air 816 by driving the piston to a predetermined location, which may be determined by a computing system. In other embodiments, a user may enter a desired pressure for the receptacle to be pressurized to.

Additionally, the biological sample 806 may be in solid, liquid, or gaseous form. When the biological sample is placed into the receptacle 804, VOCs which are present in the biological sample are released into the air inside the receptacle 804. In particular embodiments, the biological sample undergoes an extraction process to maximize the VOCs released from the biological sample. The VOC extraction process is discussed in detail below. This air comprising VOCs from the biological sample ("odor-soaked air") can be pushed through into the flow path into the sniffing port. Accordingly, the olfactometer system is capable of receiving biological samples in solid, liquid, or gaseous states.

VOC Extraction

VOC extraction comprises extracting the VOCs from the biological sample. A VOC extraction process may optionally be performed as part of sample preparation prior to testing. In particular embodiments, VOCs may be extracted through one or more of: heat, pressure, turbulence (e.g. by shaking), or air flow. In particular embodiments, the storage component may withstand temperatures of up to 300 °C. In particular embodiments, a biological sample is heated to 24 °C-140 °C. In particular embodiments, the VOCs are extracted when the sniff from a detection animal causes turbulence in the biological sample. In particular embodiments, VOCs are extracted, using an olfactometer, by creating a vacuum in a receptacle containing the biological sample and then driving a piston into the receptacle, thereby increasing the pressure in the receptacle. Although this disclosure describes example procedures for VOC extraction, this disclosure contemplates any suitable method for VOC extraction.

In particular embodiments, the testing facility receives a biological sample (e.g., a mask) which is held in a sealed, storage component (e.g., a jar), at a first volume of air. VOCs reside in the biological sample (e.g., a mask), and VOCs which are released from the biological sample are in the air space of storage component. When the seal of the storage component is opened, air diffusion occurs and the VOCs exit the storage component and may be released via a flow path to a sniffing port.

After a desired amount of VOCs are released to a sensor (e.g., a detection animal), by pushing the plunger in the receptacle to extract the sample, the olfactometer system may drive the piston 812 back to its original position, e.g., a position indicated by 822. When the piston is pulled back, the volume of air is returned back to the first volume and restored to atmospheric pressure. In particular embodiments, the system may add sterile air into the receptacle 804. In particular embodiments, the air pressure required to pull the piston back to its original location (e.g. location 822 of FIG. 8) requires approximate six times the amount of air required to push the piston on. In particular embodiments, the air pressure required to pull back the piston changes depending on the air volume in the receptacle, wherein the air volume in the container changes over time as the piston is pulled back. In particular embodiments, the location 822 changes over time. The stream of external sterile air into the container is calculated in a manner to ensure that the pressure on the piston stays constant by increasing the outer air volume stream.

After a period of time, the VOCs will be re-released into the airspace of the receptacle. The phenomenon of this re-release of VOCs is an example of solid phase equilibrium. This re-release of VOCs from the biological sample results in the sample being “re-charged” and ready to be used in a next run. In particular embodiments, this “re-charged” sample may be used in a different run—for example, to repeat the run and expose the sample to the same detection animal, or to expose the sample to a different detection animal.

Olfactometer Operation

In certain embodiments, the olfactometer system comprises a plurality of valves, e.g. 818 and 820, which may be opened or closed. FIG. 8 depicts valve 818 in an open position and valve 820 in a closed position. In an example embodiment, the olfactometer system drives the piston 812 to cause air from the receptacle to travel through the open valve 818 to the sniffing port 810 via the flow path 808. In particular embodiments, the flow rates used to expose the sample to a detection animal are lower than the flow rates used in human applications.

Optionally, a plurality of valves may be open at the same time, and a plurality of pistons each corresponding to a receptacle may be activated at the same time, thus driving a plurality of samples into the sniffing port. A benefit of this method of operation is that a plurality of samples (e.g., a “pool”) may be exposed to a detection animal at a first time, thus increasing the efficiency of disease-detection. Upon a determination that a pool of samples has a positive detection event, the olfactometer system can individually expose each biological sample to the detection animal to determine the one or more biological samples which contain cancerous VOCs.

In particular embodiments, two or more biological samples may be mixed to create a new sample for training or maintenance purposes. In particular embodiments, the olfactometer system may expose a plurality of samples to a detection animal for training. In particular embodiments, a mixed sample may be created by lab personnel. In particular embodiments, one or more known biological samples (e.g. known biological samples with lung cancer) may be mixed for training.

In certain embodiments, there are one or more sensors proximate to the sniffing port. Example sensors include: a biosensor such as a detection animal (e.g., a canine), a biochemical sensor, or electrical sensors. In particular embodiments, a sensor proximate to the sniffing port can measure the total and/or specific amount of VOCs which is delivered to the sniffing port. This sensor simultaneously has a quality control function by ensuring that the correct amount of VOCs, and a correct amount of odor-soaked air, have been delivered to the sensor(s). In particular embodiments, sensors may comprise one or more gas sensors, including a chemical or electrical sensor that can measure a total amount of VOCs or detect the presence of a particular VOC. In particular embodiments, the gas sensor measures the volume of the exposed sample, the exposed sample comprising both VOCs and air. In particular embodiments, the gas sensor can detect a quality or quantity of an inorganic gas, the inorganic gas which is correlated to a quality or quantity of a biological sample. In particular embodiments, data from one or more gas sensors is input into one or more ML-models for calculating a confidence score.

In particular embodiments, the olfactometer system 80 performs a cleaning cycle using an automated process, resulting in increased efficiency and throughput of sample testing. A cleaning cycle is performed using gas (e.g., compressed air) from a gas source 824. The gas source 824 flows through valve 826. FIG. 8 depicts valve 826 in a closed state. However, during an example cleaning cycle, the system may close the valves between the sniffing port 810 and the receptacles (e.g., 804), and open valve 826 to run clean air through the system. The clean air flushes VOCs out of the sniffing port and follows a path ending at the exhaust line 828.

Figure 9A:
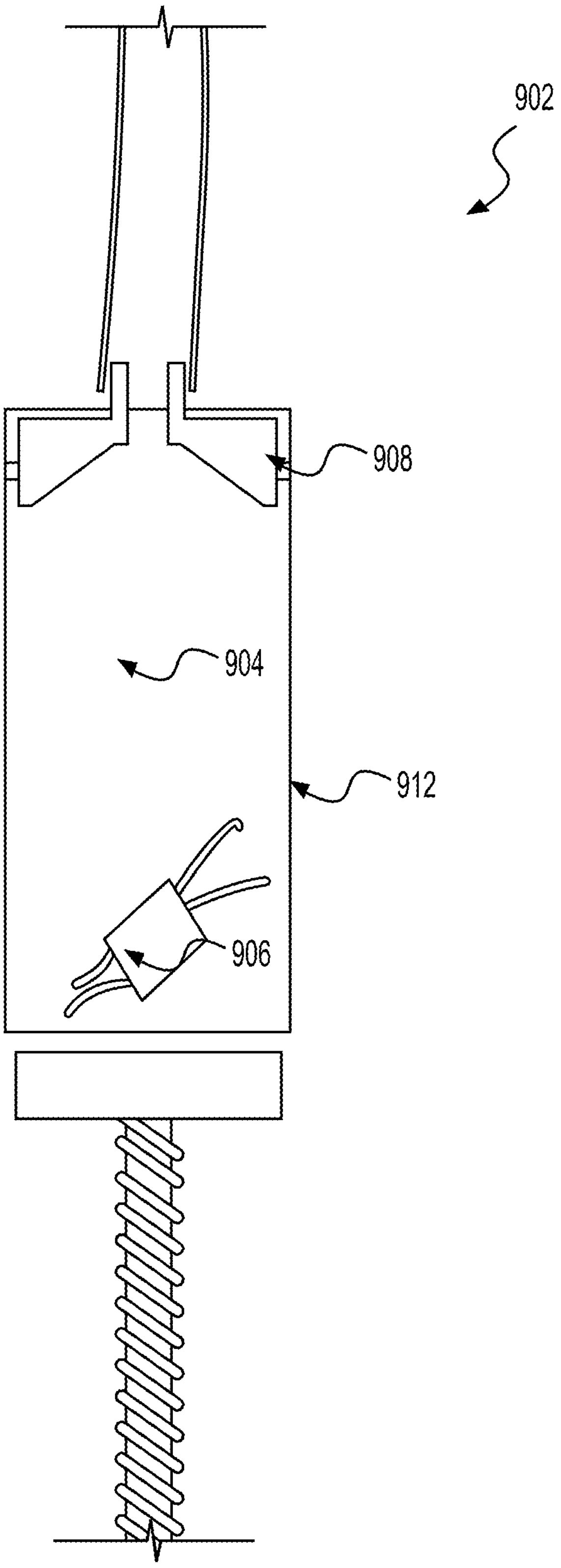
FIGS. 9A-9B illustrate an example odor detection system.
Figure 9B:
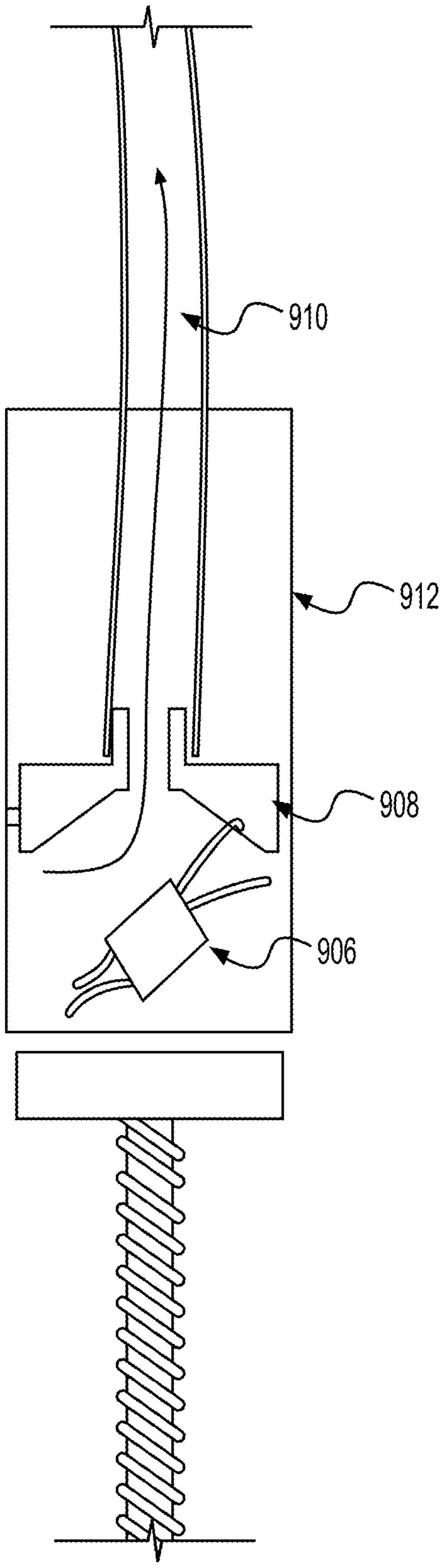

FIGS. 9A and 9B illustrate another example embodiment 902 of a receptacle comprising a piston. FIG. 9A depicts an embodiment wherein the odor-soaked air 904 is not being pushed out of the receptacle 912. The odor-soaked air 904 comprises VOCs from biological sample 906. FIG. 9A depicts piston 908 in a non-activated position. FIG. 9B depicts the piston 908 in an activated position. While in an activated position, the piston is driven into the receptacle 912, thereby causing the odor-soaked air from the sample to travel to the sniffing port through flow path 910. The odor-soaked air may be controllably pushed out of the receptacle 912, thereby causing a predetermined amount of air to travel to the sniffing port, with zero dilution.

It is evident from FIGS. 9A and 9B that the piston 908 is at a first location in the receptacle 912 while in a non-activated state, and at a second location in an activated state.

Figure 10:
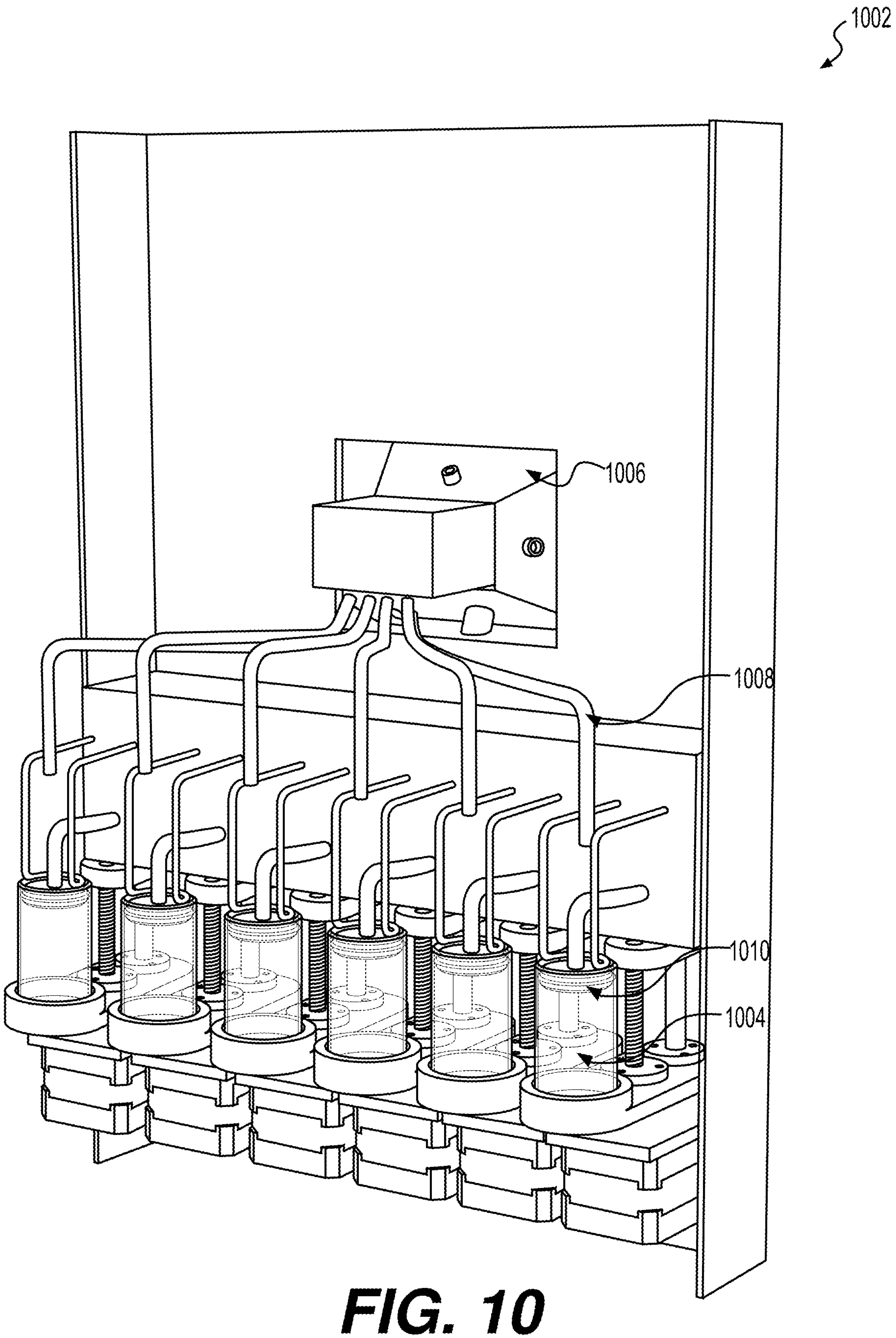
FIG. 10 illustrates an example odor detection system.

FIG. 10 depicts an example view of an olfactometer system 1002. In an example embodiment, the receptacles 1004 operable to hold a biological sample are located in a first room and the detection animal operates in a second room. A sniffing port 1006 is contained in the second room, and the sniffing port is connected via a plurality of flow paths 1008 to receptacles in the first room. As described in the example embodiments above, odor-soaked air from the receptacles 1004 may be delivered to a sniffing port by driving a piston 1010 into the receptacle, thereby causing a predetermined amount of gas to travel through a flow path 1008 to the sniffing port.

In particular embodiments, the receptacle 1004 is formed of inert material such as stainless steel. In particular embodiments, the sealed receptacle may be connected to the olfactometer system without exposing the biological sample to the environment. In particular embodiments, a tube connected to the storage component may be attached to a fitting of the olfactometer system.

Figure 11B:
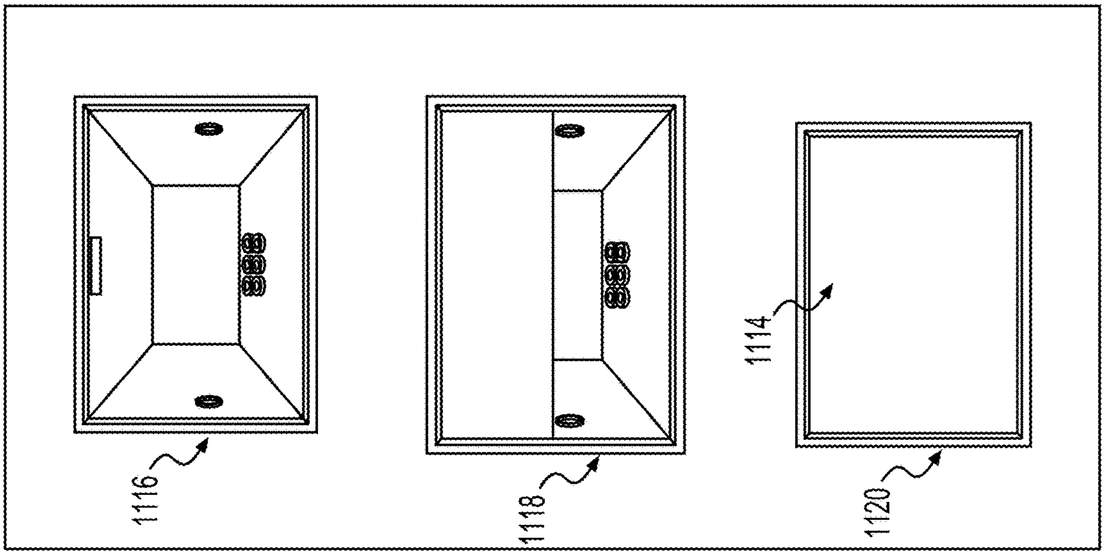
FIGS. 11A-11B illustrate an example odor detection system.
Figure 11A:
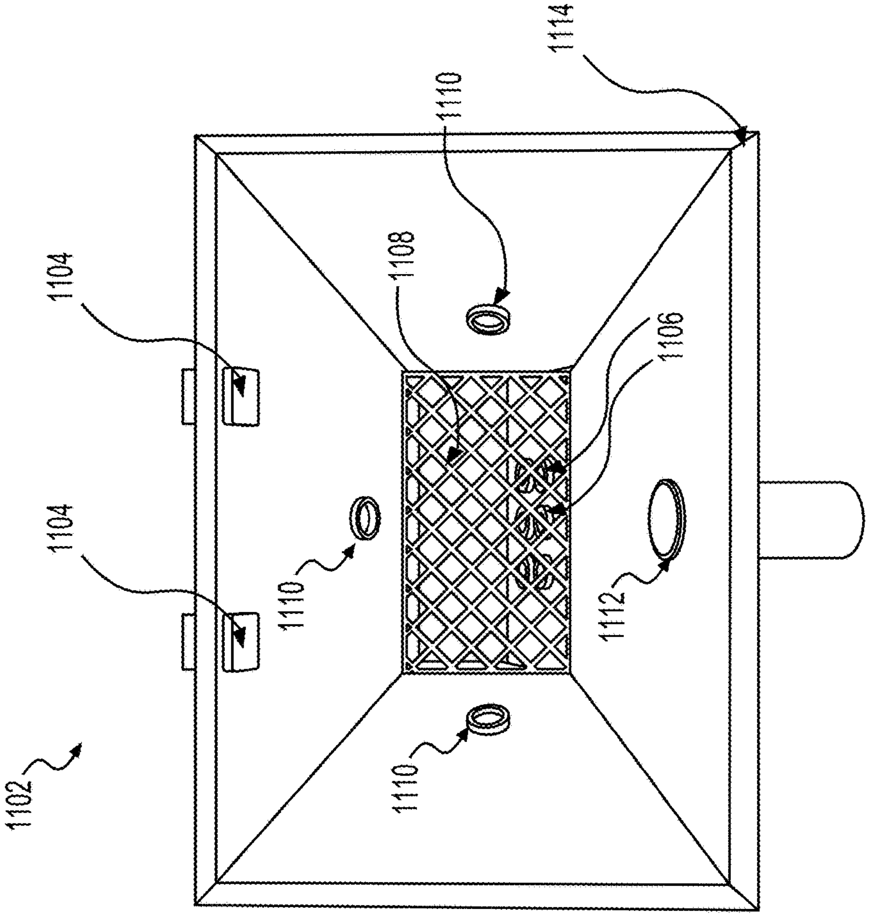

FIGS. 11A-11B show views of a sniffing port. In FIG. 11A, the sniffing port 1102 comprises two infrared sensors 1104, which are operable to measure the length of a sniff of the detection animal. In particular embodiments, the ML system interprets a sniff of at least 200 milliseconds (ms) as constituting a valid sniff. In particular embodiments, if the detection animal removes its nose early, e.g., before a predetermined time interval of 200 ms for example, then the flow path from the biological sample to the sniffing port is stopped. In particular embodiments, if the detection animal sniffs the sample for more than a predetermined time, e.g., 300 ms, then the olfactometer system will push more odor from the receptacle holding the biological sample, to the sniffing port. The olfactometer system pushes transports odor from the receptacle holding the biological sample, to the sniffing port, through low pressure inlets 1106. FIG. 11 depicts six low pressure inlets behind a replaceable grill 1108. Although this disclosure describes a system with a particular number of low-pressure inlets, this disclosure contemplates a system with any suitable the number of low-pressure inlets, and in particular embodiments, the number of low pressure inlets correspond to the number of receptacles operable to hold a biological sample. The replaceable grill 1108 serves to prevent the detection animal from directly touching the low-pressure inlets 1106. The olfactometer system also comprises a plurality high-pressure cleaning inlets 1110. The high-pressure cleaning inlets 1110 inject clean air into the sniffing port to clean the sniffing port between runs. Exhaust port 1112 provides a mechanism from removing air from the sniffing port. The sniffing port further comprises a mechanized door 1114, the operation of which is depicted in FIG. 11B.

FIG. 11B depicts a mechanized door 1114 of the sniffing port. The mechanized door 1114 may be opened or closed. In particular embodiments, the mechanized door remains close unless active testing is being formed. The closed door prevents contaminants from the external environment or the laboratory environment from traveling inside the sniffing port. 1116 depicts the mechanized door 1114 in a fully open state, 1118 depicts the mechanized door 1114 in a half open state, and mechanized door 1120 depicts the mechanized door 1114 in a fully closed state.

Figure 12:
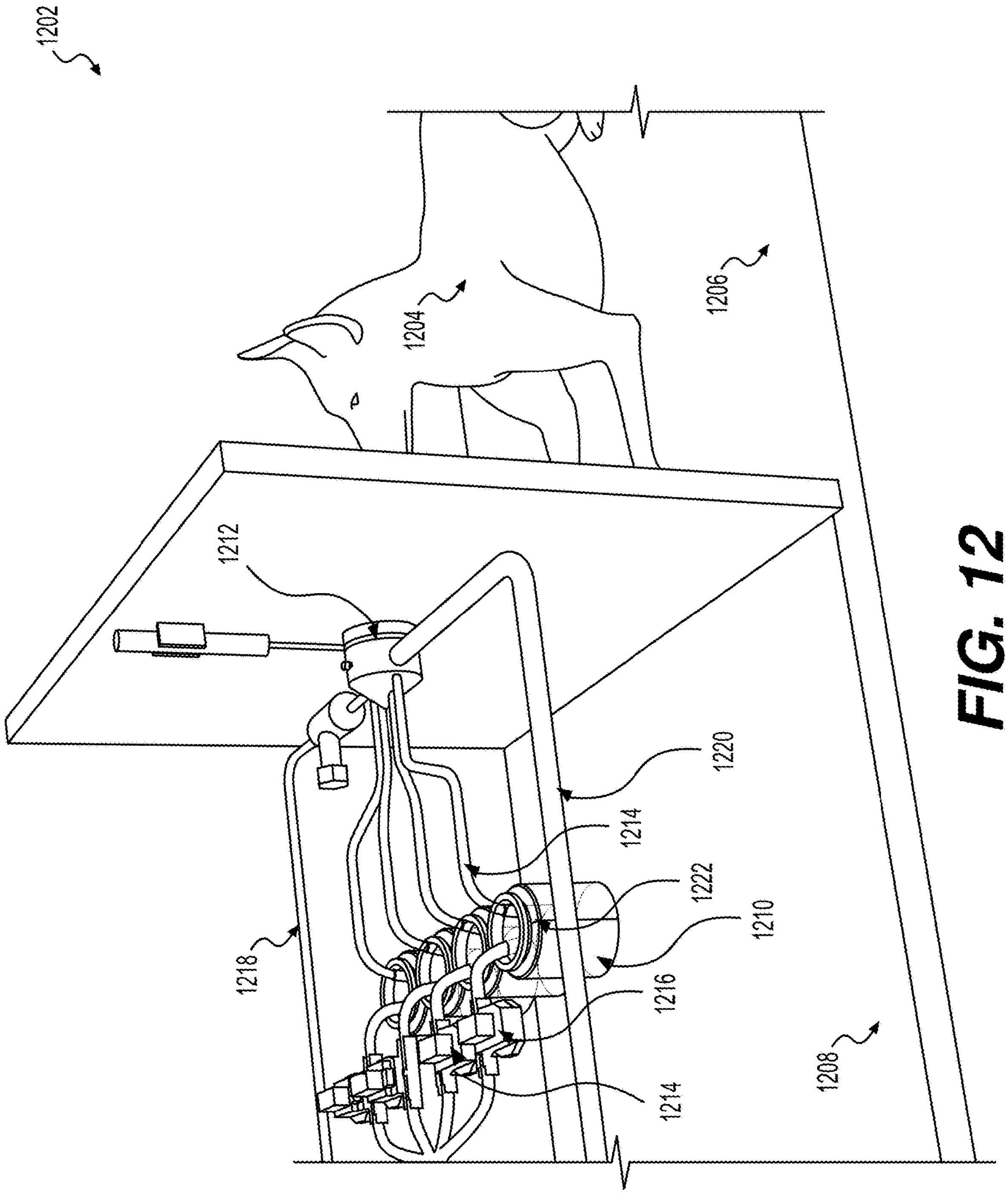
FIG. 12 illustrates an example odor detection system.

FIG. 12 depicts an example view of an olfactometer system 1202. In particular embodiments, the detection animal 1204 is in a first room 1206, a sniffing port (not pictured) is located in the second room 1208, and the receptacles 1210 are in a second room. An example portal to the sniffing port is depicted as portal 1212. The receptacles are connected to the sniffing port via a plurality of flow paths 1214. In an example embodiment, the physical separation between the first room and the second room enables the clinical facility to continuously load biological samples in the second room 1208 while the detection animal performs continuous testing in the first room 1206.

In an example operation, a biological sample is placed into each receptacle 1210, and the receptacle 1210 is attached to the olfactometer system 1202. In particular embodiments, the olfactometer system runs a cleaning step. In particular embodiments, during the cleaning step, valves (e.g. 1216) to the receptacles are in a closed position, and air is flushed through flow paths 1218 and 1220, as well as through the portal 1212 to the sniffing port. In particular embodiments, air passes through or more of an active carbon filter or a humidity trap filter before it is pushed into the olfactometer system.

During a run, one or valves 1216 may be opened. For example, during a test comprising pooled samples, a plurality of valves 1216 may be opened to allow odor-soaked air from a plurality of receptacles to be delivered to the sniffing port. In other embodiments, only one valve is opened at each time. Further, during a run, the piston 1222 is driven into the receptacle, thereby forcing odor-soaked air out of the receptacle and through the flow path.

Disease-Detection System

Figure 13:
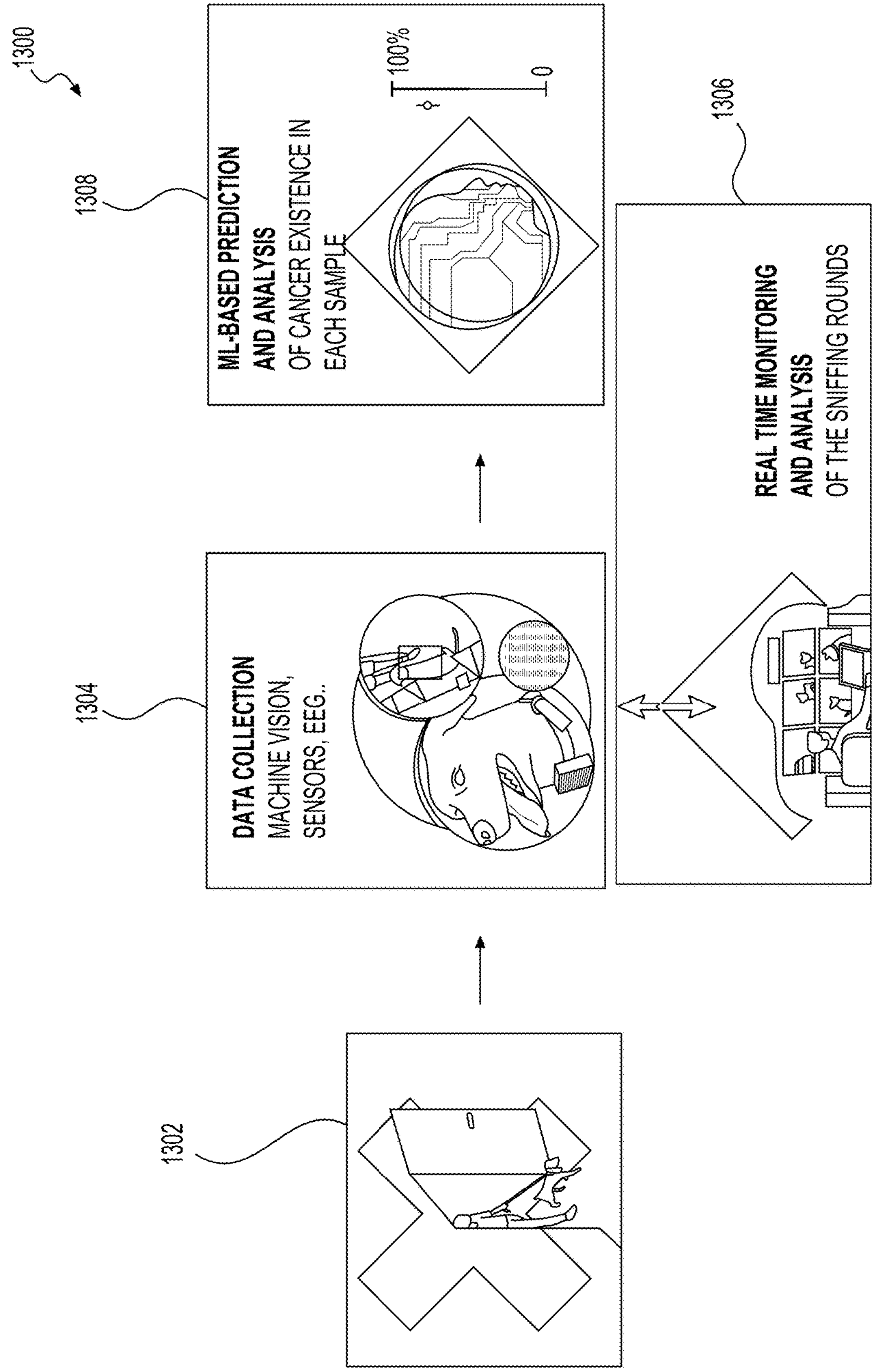
FIG. 13 illustrates an example disease-detection method.

FIG. 13 illustrates an example method 1300 of the disease-detection system, which comprises a data collection step 1304, a real-time monitoring and analysis step 1306, and a ML-based prediction and analysis step 1308. In particular embodiments, disease-detection system may further comprise one or more additional computing components, including a monitoring component and an operational component.

The method 1300 may begin at step 1302 with a detection animal entering a screening room. In one embodiment, the screening room contains a plurality of biological samples. In another embodiment, the screening room contains one or more sniffing ports which are coupled to one or more receptacles contains one or more biological samples.

At step 1304, the disease-detection system collects data from one or more sensors comprising: one or more behavioral sensors, one or more physiological sensors, one or more neurological sensors, or one or more operational sensors. In particular embodiments, the sensors measure one or more of: animal behavior, animal physiological patterns, or animal neurological patterns.

In particular embodiments, behavioral sensors collect data on a behavior of the detection animal. In particular embodiment, behavior may include a body pose of detection animal. As an example and not by way of limitation, body poses include, but are not limited to, standing at next to the sniffing port, sitting next to the sniffing port, or looking at a handler. As an example and not by way of limitation, animal behavior may include: repeatedly sniffing a particular receptacle or long sniffs at a particular receptacle, which may indicate that the detection animal is indecisive as to the status of the biological sample. Animal behavior may include the amount of time an animal investigates a particular receptacle, and the amount of time it takes for an animal to indicate it found a target odor after investigating a receptacle. Animal behavior may also include the speed at which the detection animal walks between sniffing ports and acceleration data associated with the detection animal walks between the sniffing ports. In particular embodiments, data is collected on one or more of: the duration of a sniff (e.g. the length of time a detection animal sniffs the biological sample), the number of repeated sniffs, the time between a sniff and a signal, or the time it takes the canine to signal. In particular embodiments, animal behavior comprises features of a sniff which are measured by one or more audio sensors. As an example and not by way of limitation, features of a sniff comprise one or more of a sound, intensity, or length of a sniff. Although this disclosure describes obtaining certain behavioral data as inputs into a ML-model, this disclosure contemplates obtaining any suitable type of behavioral data to be input into a ML-model.

In particular embodiments, environmental sensors collect data on one or more conditions of the screening room, including at locations near sniffing port. As an example and not by way of limitation, environmental sensors are operable to receive data associated with the testing room and/or the sniffing port(s), such as the temperature, humidity, noise level, air flow, and air quality of the screening room or the sniffing port(s).

In particular embodiments, the data collection step 1304 comprises collecting data from one or more physiological sensors comprising one or more of: heart rate monitor, heart rate variability monitor, temperature sensor, galvanic skin response (GSR) sensor, sweat rate sensor, or a breath rate sensor.

In particular embodiments, the data collection step 1304 comprises collecting data from one or more neurological sensors comprising one or more of: one or more electroencephalogram (EEG) sensors, one or more functional near-infrared spectroscopy (fNIR) sensors, one or more functional magnetic resonance imaging (fMRI) scanners, or one or more magnetic resonance imaging (MRI) scanners.

In particular embodiments, the data collection step 1304 comprises collecting data from operational sensors. In particular embodiments, the operational sensors comprise one or more of: sensors in the olfactometer, sensors for animal management (e.g., a RFID card which identifies a particular canine), and sensors for sample management (e.g., a QR code scanner which scans a unique QR code associated with each biological sample).

In particular embodiments, the data collection step 1304 comprises receiving non-behavioral data such as the family medical history, patient medical history, patient age, patient gender, or patient demographical data.

The method 1300 may continue at step 1306 wherein a person or a machine performs real-time monitoring and analysis of one or more of the behavioral sensors, physiological sensor, or environmental sensors, during one or more of the rounds of animal investigation. In particular embodiments, the real-time monitoring and analysis may be done on one detection animal; in other embodiments, the real-time monitoring and analysis may be done on a pack of detection animals. In particular embodiments, each detection animal has a monitoring algorithm (e.g., an ML-model operable for a monitoring function) calibrated to that particular detection animal. In particular embodiments, an animal investigation is a sniffing round in which a canine sniffs the receptacles in the screening room. In particular embodiments, a human or machine monitors the testing to ensure standard operating procedures are followed by the detection animal and/or its human handler. In particular embodiments, step 1306 includes one or more actions performed by a computing component of the disease-detection system. As an example and not by way of limitation, the computing component may comprise a real-time monitoring program which monitors a condition (e.g., temperature) of the screening room and alerts the lab manager immediately upon detection of an out-of-range condition. As used herein, "lab manager" refers to one or more persons responsible for setting up a run (either physically or through a machine), or overseeing a run.

In particular embodiments, the disease-detection system monitors parameters and provides alerts for certain parameters in real-time regarding certain abnormalities (e.g., an environmental abnormality or a behavioral abnormality) or failures within the test procedure. As an example and not by way of limitation, real-time monitoring and analysis comprises receiving and analyzing environmental sensor data (e.g. temperature, humidity range, etc.), and alerting a lab manager in if one or more of predetermined environmental data is out of range. As an example and not by way of limitation, the system may alert a lab manager upon an indication that a sensor is not functioning properly. As an example and not by way of limitation, the real-time monitoring and analysis comprises monitoring a particular action of a detection animal (e.g., a sniff at a sniffing port) to determine whether the action meets a predetermined criteria (e.g., a duration of a sniff).

In particular embodiments, the system monitors the behavior of the detection animal for behavioral abnormalities (e.g. a long duration of a sniff without any positive or negative indication of a disease state). In particular embodiments, if the measured action does not meet a predetermined criteria, the system provides an alert to the lab manager. In particular embodiments, step 1306 comprises monitoring that the received sensor data is valid. In particular embodiments, step 1306 comprises monitoring animal behavior for any drift of animal performance during a during test run. In particular embodiments, behavioral drift may be monitored by either a ML-model or a computing component of the disease-detection system. In particular embodiments, the parameters may further include a physiological condition of a dog, such as one or more of: a heart rate, a heart rate variability, a temperature, a breath rate, or a sweat rate. The parameters may further include sample storage conditions, such as temperature and humidity. In particular embodiments, the system may alert the lab manager in real-time, after a positive detection event. In particular embodiments, the disease-detection system comprising the biological samples, the detection animals, the laboratory facilities, and the storage facilities are continuously monitored, and alerts are pushed to a person when one or more parameters is out of range. In particular embodiments, if an alert affects a clinical test, an alert will pop up on the monitoring screen and will require a lab manager to take action.

In particular embodiments, the disease-detection system monitors every sniff of the detection animal and based on predetermined thresholds set as a valid sniff (e.g., a time period of 200 ms), the system provides alerts in real-time when a sniff doesn't meet the predetermined threshold.

The disease-detection system records certain activities performed in the sniffing rooms. For example, the activities may include the behavior of the handler of the detection animal. Further, the disease-detection system records all signals received from the canines, which may include physiological data from one or more sensors and animal behaviors such as an animal pose.

In particular embodiments, the real-time monitoring and analysis 1306 ensures that each test run is performed under predetermined conditions (e.g., within a predetermined range of temperature, light level, sound level, air particulate level, wherein the behavior of the detection animal meets a predetermined criteria, wherein there are no behavioral abnormalities, etc.), but data from the real-time monitoring and analysis 1306 is not directly input into the ML-based prediction and analysis 1308.

The method 1300 may continue at step 1308 wherein the disease-detection system uses one or more ML-models to perform ML-based prediction(s) based on one or more of the: behavioral data, physiological data, neurological data, or patient data received from data collection step 1304. As an example but not by way of limitation, a ML-body may receive animal behavior data, e.g. a body pose, and patient data as an input.

In particular embodiments, the disease-detection system comprises one or more ML-models. In particular embodiments, the one or more ML-models include: one or more ML-models for a particular detection animal (e.g., a dog-specific ML-model), one or more ML-model for a plurality of detection animals (e.g., a dog pack-specific ML-model), one or more test stage-specific models (e.g., a ML-model for a first stage of a test, a ML-model for a second stage of a test), one or more ML-models trained on disease states (e.g. a positive or negative determination of cancer), one or more ML-models trained on cancer types (e.g., breast cancer, lung cancer, colon cancer, prostate cancer), one or more ML-models trained on cancer stages (e.g., stage 1, stage 2, stage 3, or stage 4), or one or more neurological-based ML-models, or one or more monitoring ML-models (e.g., monitoring the behavioral drift of a detection animal). In particular embodiments, the one or more ML-models may receive one or more of: behavioral data, physiological data, neurological data, or patient data. In particular embodiments, a test run comprises a plurality of stage. As an example and not by way of limitation, a first stage of a test may comprise a plurality of detection animals performing a run. As an example and not by way of limitation, a second stage of a test may comprise aggregating the scores from the first stage of the test. Although this disclosure describes and illustrates particular steps of test, this disclosure contemplates any suitable steps for a test, the steps which may occur in any suitable order.

In particular embodiments, once the test run has finished, the disease-detection system may give recommendations as for the lab results of each sample participating, with the ability of the lab personnel to intervene and alter the results based on the data they are presented with. In particular embodiments, the ML-based disease-detection model provides both a lab result (e.g., a ML-based result of a disease state and an associated confidence interval) as well as the dog result prediction (e.g., a particular behavior of a dog which indicates a particular disease state).

In particular embodiments, the ML-based disease-detection model generates feature representations based on one or more of behavioral responses, physiological responses, or neurological responses of the detection animal exposed to a biological sample. In particular embodiments, the ML-based disease-detection model further receives patient data. In particular embodiments, the one or more ML-models are created through offline learning. In particular embodiments, the one or more ML-models are created through online learning. In particular embodiments, the ML-based disease-detection model may store black box features without any interpretation.

In particular embodiments, one or more ML-based disease-detection models are trained on indications or signals of a detection animal associated with a biomarker (e.g., a particular scent of a VOC). As an example and not by way of limitation, indications from a detection animal may comprise one or more of: a sitting position, a lying position, or looking at the animal handler to indicate a positive disease-detection event. As an example and not by way of limitation, signals such as heart rate, heart rate variability, and temperature of the detection animal may change upon different sample indications as a result of the anticipation for a reward. Furthermore, signals generated by neurosensory collection (e.g., by EEG, fNIR, fMRI, or MIR) may change upon one or more of: a positive or negative cancer state, a type of a cancer, or a stage of a cancer.

In particular embodiments, a validation step is performed to measure the performance of the one or more ML-models by comparing the determination outputted by the ML-based disease-detection model, with the known disease state of a training sample. In particular embodiments, the ML-based disease-detection model is validated by: exposing one or more training samples to one or more detection animals, wherein each of the training samples has a known disease state, receiving sensor data associated with one or more detection animals that have been exposed to the training sample, calculating one or more confidence scores corresponding to one or more disease states associated with the training samples, and determining a number of inferences by the ML-based disease-detection model that are indicative of the particular disease state.

In particular embodiments, the known disease state of the training sample may be obtained through a liquid biopsy. As an example and not by way of limitation, the discrepancy between the target disease state and the disease state detected by the ML-model is measured, and the training method described herein is re-performed until a predetermined number of iterations is reached or until the a value associated with the discrepancy reaches a predetermined state. In particular embodiments, the system iteratively updates the parameters of the ML-based disease-detection model using an optimization algorithm based on a cost function, wherein the cost function measures a discrepancy between the target output and the output predicted by the ML-based disease-detection model for each training example in the set, wherein the parameters are repeatedly updated until a convergence condition is met or a predetermined number of iterations is reached. In particular embodiments, the system outputs a trained ML-based disease-detection model with the updated parameters.

In particular embodiments, a positive disease-detection event may result in confirming the positive disease-detection of the biological sample through another method, such as by a genomic test. In particular embodiments, the additional test is performed upon a determination that the confidence score is below a predetermined threshold. In particular embodiments, the genomic test is performed using a liquid biopsy from the patient.

In particular embodiments, an EEG device worn by a detection animal may be used as an additional verification step. In particular embodiments, the EEG data indicates the origin of cancer (e.g. whether the cancer is from the breast or the lung). In particular embodiments, a neurological-based ML-model analyzes the EEG response of a detection animal after it has been exposed to a particular odor.

In particular embodiments, one or more neurological-based ML-models are developed based on a detection animal's neurological response to a target odor. For example, one or more ML-models may be developed to detect a disease state (e.g. positive or negative cancer state), a cancer type, or a cancer stage. In particular embodiments, a neurological-based ML-model may receive data comprising one or more of behavior data, physiological data, or patient data. In particular embodiments, non-neurological data, such as operational data associated with the olfactometer (e.g., a start and end time of odor release), behavioral data, and physiological data (e.g., a heart rate) are also collected during an EEG or other neurological-based test. In particular embodiments, the detection animal is not trained for an odor detection task. In particular embodiments, the neurological-based ML-model receives neurological data (e.g., EEG data), as well as data from an olfactometer. In particular embodiments, data from the olfactometer comprises a timeline indicating the time(s) that a particular odor is exposed to the detection animal. In particular embodiments, the neurological-based ML-model receives data from an accelerometer worn by the detection animal during testing (and including during the exposure event). In particular embodiments, the neurological-based ML-model receives behavioral data and physiological data from the sensors described herein.

In particular embodiments, the olfactometer comprises a sniffing port which is coated with Teflon, or a Teflon-based material to facilitate deodorization and reduce signal interference from conductive materials such as stainless steel. In particular embodiments, the sniffing port may be formed of glass. In particular embodiments, the testing area is formed of a Teflon-based material. In particular embodiments, the detection animal is on a Teflon-based platform (e.g., a bed of an detection animal) during testing. Although this disclosure describes suitable materials for an olfactometer system in a particular manner, this disclosure contemplates any suitable materials for the olfactometer system, and in particular, the sniffing port.

In particular embodiments, the neurological response comprises a trend in an EEG. In particular embodiments, a neurological-based ML-model may be trained on correlations between a detection animal's neurological response and a target odor. In particular embodiments, the neurological-based ML-model outputs one or more of: a positive or negative state (e.g., a positive or negative cancer indication), a cancer type, or a cancer stage. In particular embodiments, neurological data is input into the ML-based disease-detection model described herein.

In particular embodiments, the ML-based disease-detection model calculates a confidence prediction interval according to a statistical calculation. Additionally, the ML-model estimates the probability of cancer for the sample, along with its confidence prediction interval. Based on it, the algorithm simplifies these measurements to: predicted disease state and its confidence score.

Figure 14:
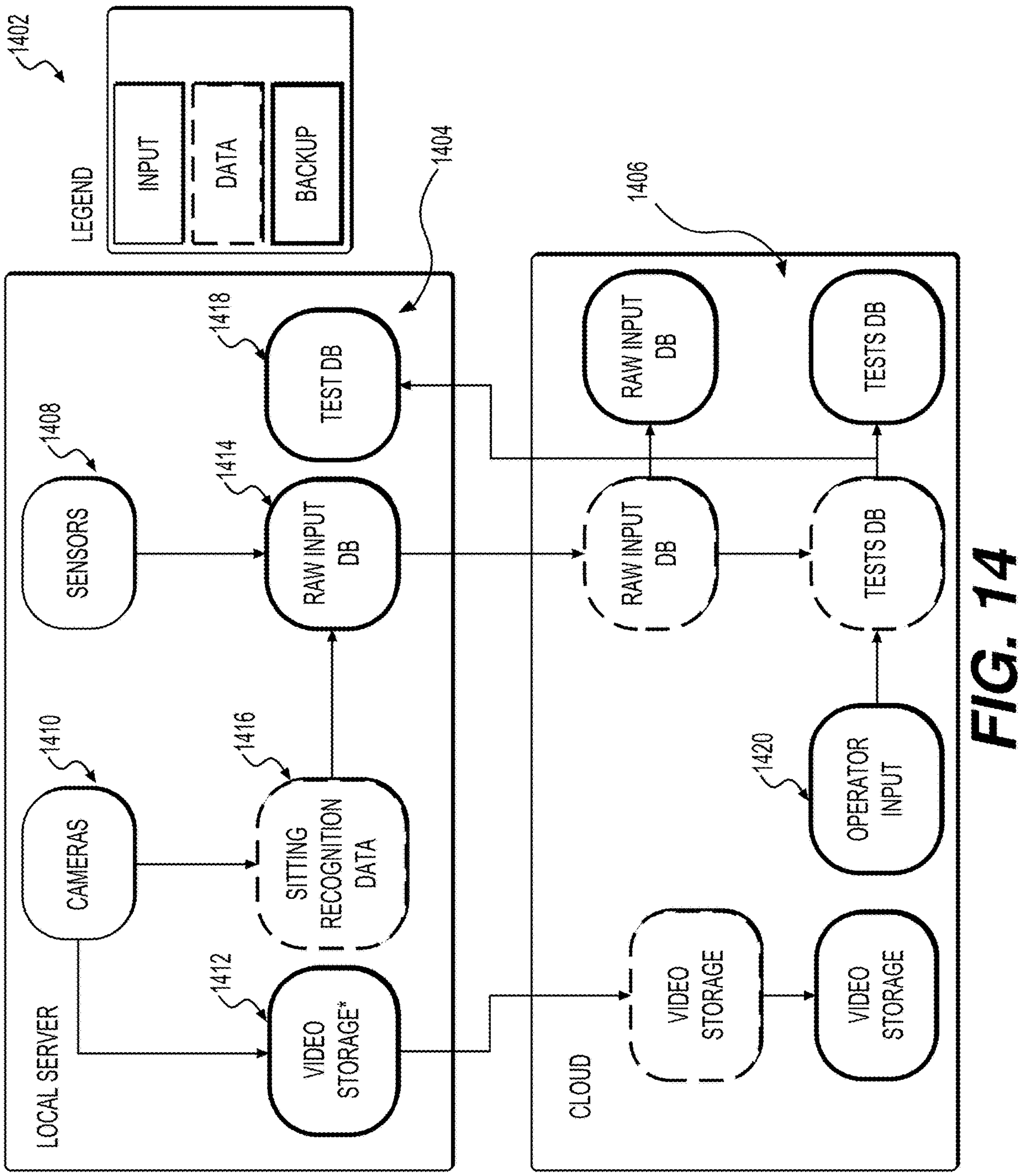
FIG. 14 illustrates an example computing system.

FIG. 14 depicts an example data flow of the disease-detection system 1402. The system comprises data stored on a local server 1404 and a cloud 1406. In particular embodiments, sensor data, video data, and operator input is streamed into the system in real time. In particular embodiments, operator input 1420 is performed by a lab manager. For example, sensor data from one or more sensors 1408 may contain one or more of: sniff events for each detection animal and the associated sniffing port(s), movements (e.g., a walking speed or an acceleration) of the detection animals, and laboratory conditions. The sensors 1408 may comprise one or more of the behavioral, physiological, or neurological sensors described herein. Further, camera/video data from one or more cameras 1410 may comprise information related to animal behavior and animal pose. For example, an animal pose may comprise a sitting or standing position of an animal. It may also comprise whether the animal looks at its handler. Animal behavior may comprise sniffing behaviors or the animal behavior in the lab (e.g. the speed at which the animal walks). Videos are temporarily stored at a video storage location 1412 at local server and before they are transferred to the cloud 1406. In particular embodiments, data comprising one or more of: environmental data, operational data, and lab manager inputs (e.g., run data), is also stored on the cloud 1406. In particular embodiments, operator input 1420 is stored on the cloud 1406. In particular embodiments, operator input 1420 comprises one or more of: family medical history, patient medical history, patient age, patient gender, or patient demographical data. In particular embodiments, a sitting pose is indicative of a positive detection event, and corresponding sitting recognition data 1416 is input into raw input database 1414. The system may further receive inputs into raw input database 1414 which comprise sensor data discussed herein, such as from one or more of: behavioral sensors or physiological sensors. In particular embodiments, the lab manager may input information regarding demographic data of the detection animal, such as the age, sex, or breed of the detection animal. In particular embodiments, the lab manager may input information regarding the patient, such as one or more of: family medical history, patient medical history, patient age, patient gender, or demographical data of the patient. The inputs may further comprise information about the number of detection rounds a detection animal has performed. The rounds data comprise the number of exposures of the detection animal to a biological sample.

Tests database 1418 comprises data about the resources (e.g., the samples, dogs, lab manager, animal handler, lab manager, and the tests). The tests database is formed by processing the raw input data as well as the data input by a user (e.g., a lab manager).

Machine-Learning Architecture

Figure 15:
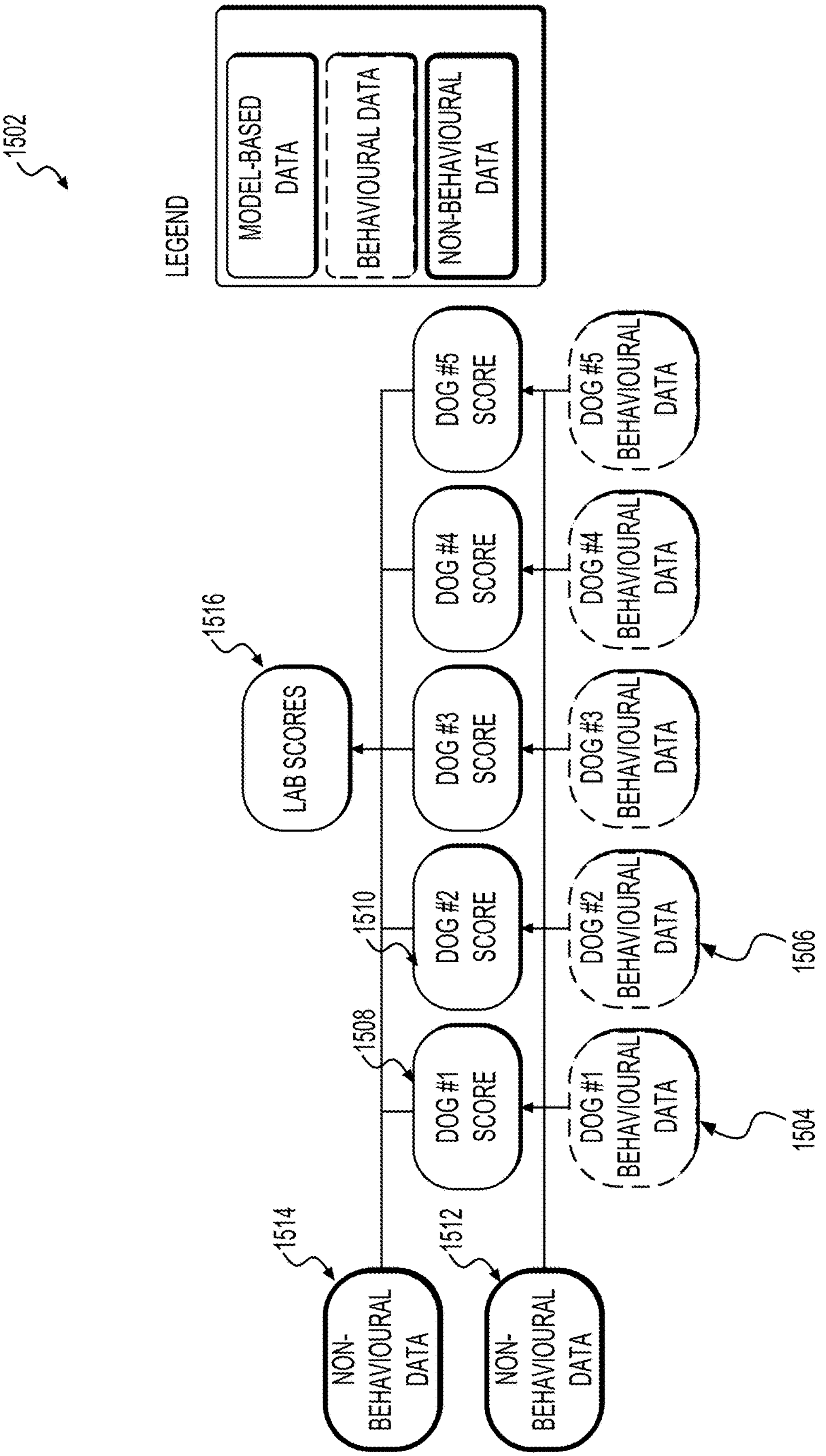
FIG. 15 illustrates a diagram of an example machine-learning (ML) architecture.

FIG. 15 illustrates an example of a model 1502 of the disease-detection system utilizing a stacked learning approach which is suitable for predicting a lab result. This architecture addresses the prediction problem in an hierarchical way, where a dog-specific predictive model is fitted for each detection animal, e.g. a dog, and then the output of the dog-specific predictive models is the input of the lab-result ML-model.

In particular embodiments, a ML-model is created for each detection animal. That is, there may be a plurality of ML-models, wherein a particular ML-model is associated with a particular animal. For example, first ML-model is fitted for Dog #1 and fitted ML-model is created for Dog #2 using relevant data (e.g. behavioral data and physiological) for each dog. Next, a lab-result ML-model is fitted for a pack of dogs (e.g., Dog #1, Dog #2, etc.), using the scores of the first ML-model, the second ML-model, etc., and non-behavioral data 1514.

As an example and not by way of limitation, Dog #1 behavioral data 1504 is input into the first ML-model (created for Dog #1), and Dog #2 behavioral data 1506 is input into the second ML-model (created for Dog #2). This method repeats for the total number of dogs. That is, dog score 1508 is determined using the behavioral data 1504 for Dog #1 and non-behavioral data 1512, and dog score 1510 is determined using the behavioral data 1506 and non-behavioral data 1512 for Dog #2. The non-behavioral data 1512 may comprise one or more of the patient data (e.g. family medical history, patient medical history, patient age, patient gender, and patient demographic data), or environmental data described herein. This respective method is performed for each respective animal. Dog #1 Score is an initial confidence score associated with Dog #1. Dog #2 Score is an initial confidence score associated with Dog #2, etc.

In particular embodiments, the non-behavioral data 1512 and 1514 may comprise data from a previous test using the systems and method described herein performed on the patient. For example, a patient undergoing cancer treatment may have a first biological sample tested using the disease-detection system, and after a period of time, have a second biological sample tested using the disease-detection system. In particular embodiments, data from prior tests on the first biological sample is already stored the disease-detection system when testing the second biological sample. In particular responses, the ML-model compares sensor and inputted data associated with the first biological sample, with sensor and inputted data associated with the second biological sample, when making a determination on a disease state and a confidence score.

Next, the fitted dog scores (e.g., 1508 and 1510) are aggregated by a lab-result ML-model, which also receives non-behavioral data 1514 as an input, to determine a lab score 1516. The non-behavioral data 1514 may comprise one or more of the patient data (e.g. family medical history, patient medical history, patient age, patient gender, and patient demographic data) and environmental data described herein. In particular embodiments, lab score 1516 is calculated based on a probability of the disease state. In particular embodiments, lab score 1516 is calculated based on a probability of the disease state and a confidence prediction interval.

Although this disclosure describes and illustrates an example ML-model of the disease-detection system utilizing a stacked learning approach comprising a plurality of steps, this disclosure contemplates any suitable ML-model for disease-detection including any suitable steps, which may include all, some, or none of the steps of the method of FIG. 15.

Figure 16:
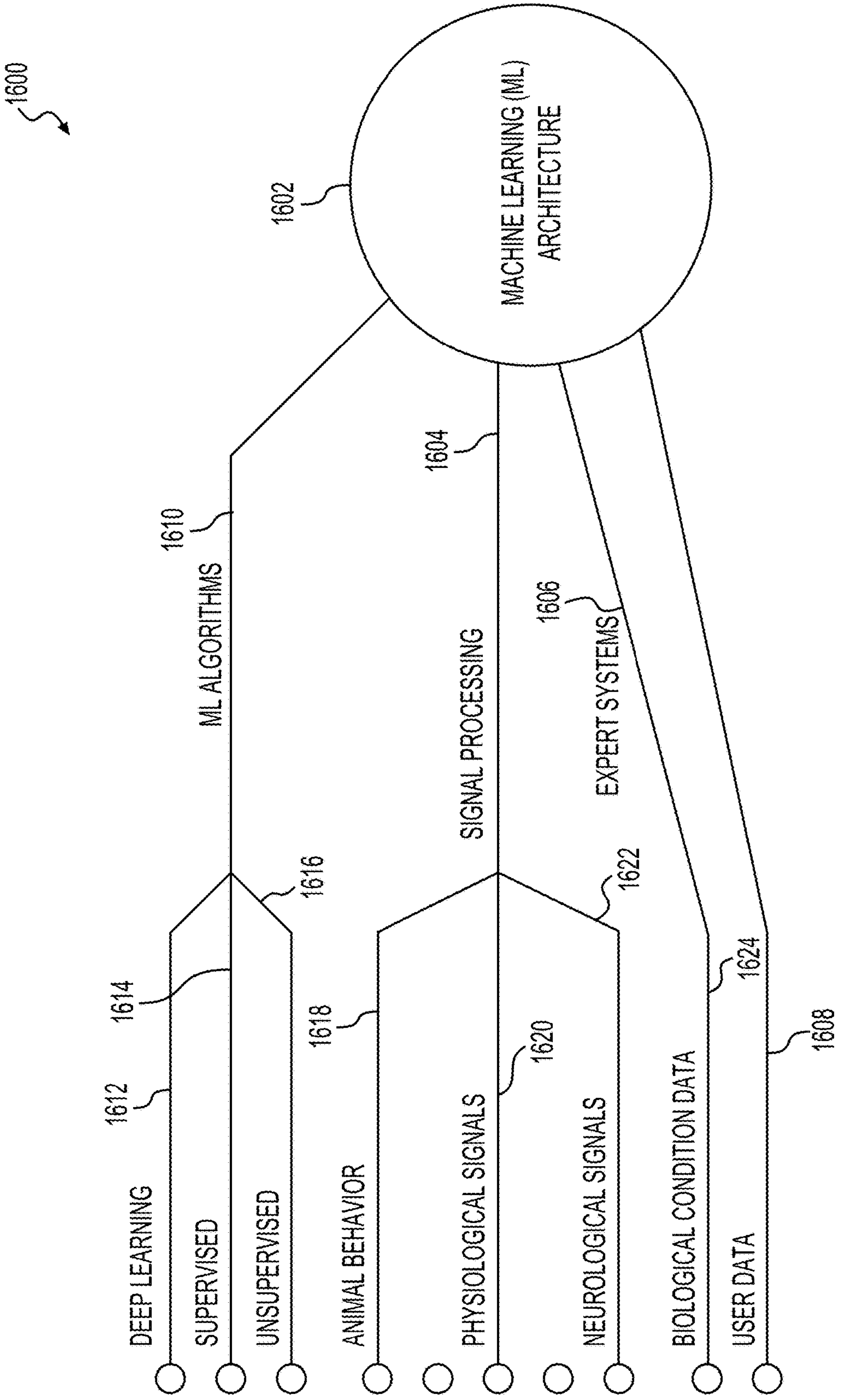
FIG. 16 illustrates a diagram of an example machine-learning (ML) architecture.

FIG. 16 illustrates a diagram 1600 of an example ML architecture 1602 that may be utilized in a disease-detection system using detection animals, in accordance with the presently disclosed embodiments. In particular embodiments, the ML architecture 1602 may be implemented utilizing, for example, one or more processing devices that may include hardware, e.g., a general purpose processor, a graphic processing unit (GPU), an application-specific integrated circuit (ASIC), a system-on-chip (SoC), a microcontroller, a field-programmable gate array (FPGA), a central processing unit (CPU), an application processor (AP), a visual processing unit (VPU), a neural processing unit (NPU), a neural decision processor (NDP), and/or other processing device(s) that may be suitable for processing various data and making one or more decisions based thereon), software (e.g., instructions running/executing on one or more processing devices), firmware (e.g., microcode), or some combination thereof.

In particular embodiments, as depicted by FIG. 16, the ML architecture 1602 may include signal processing algorithms and functions 1604, expert systems 1606, and user data 1608. In particular embodiments, the ML algorithms and functions 1610 may include any statistics-based algorithms that may be suitable for finding patterns across large amounts of data. As an example and not by way of limitation, in particular embodiments, the ML algorithms and functions 1610 may include deep learning algorithms 1612, supervised learning algorithms 1614, and unsupervised learning algorithms 1616.

In particular embodiments, the deep learning algorithms 1612 may include any artificial neural networks (ANNs) that may be utilized to learn deep levels of representations and abstractions from large amounts of data. As an example and not by way of limitation, the deep learning algorithms 1612 may include ANNs, such as a multilayer perceptron (MLP), an autoencoder (AE), a convolution neural network (CNN), a recurrent neural network (RNN), long short term memory (LSTM), a grated recurrent unit (GRU), a restricted Boltzmann Machine (RBM), a deep belief network (DBN), a bidirectional recurrent deep neural network (BRDNN), a generative adversarial network (GAN), and deep Q-networks, a neural autoregressive distribution estimation (NADE), an adversarial network (AN), attentional models (AM), deep reinforcement learning, and so forth.

In particular embodiments, the supervised learning algorithms 1614 may include any algorithms that may be utilized to apply, for example, what has been learned in the past to new data using labeled examples for predicting future events. As an example and not by way of limitation, starting from the analysis of a known training dataset, the supervised learning algorithms 1614 may produce an inferred function to make predictions about the output values. The supervised learning algorithms 1614 can also compare its output with the correct and intended output and find errors in order to modify the supervised learning algorithms 1614 accordingly. On the other hand, the unsupervised learning algorithms 1616 may include any algorithms that may applied, for example, when the data used to train the unsupervised learning algorithms 1616 are neither classified nor labeled. As an example and not by way of limitation, the unsupervised learning algorithms 1616 may study and analyze how systems may infer a function to describe a hidden structure from unlabeled data.

In particular embodiments, the signal processing algorithms and functions 1604 may include any algorithms or functions that may be suitable for automatically manipulating signals, including animal behavior signals 1618, physiological signals 1620, and neurological signals 1622 (e.g., EEG, fNIR, fMRI, or MRI signals).

In particular embodiments, the expert systems 1608 may include any algorithms or functions that may be suitable for recognizing and translating signals from detection animals and user data 1626 into biological condition data 1624. Examples of ML planning may include AI planning (e.g. classical planning, reduction to other problems, temporal planning, probabilistic planning, preference-based planning, or conditional planning.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Machine-Learning Overview

In particular embodiments, the disease-detection system comprises a plurality of ML-models. Features of the ML-model are based on one or more behavioral events (e.g., sniffing and sitting events), physiological events, neurological events in testing, or patient data. Example behavioral, physiological, and neurological events are described herein. In particular embodiments, a custom ML-model is created for each detection animal. As an example and not by way of limitation, a custom ML-model is created to analyze the behavior, physiological response, or neurological response of the detection animal during a test run. As another example, the system comprises an ML-model which calculates a dog score based on behavioral and non-behavioral inputs. As another example, the system comprises an ML-model which analyzes the physiological data from a detection animal. As another example, the system comprises an ML-model which may use data from the sensors described herein to calculate a measurement of indecisiveness in the detection animal. As another example, the system comprises a ML-model customized to monitor a behavioral drift (e.g., a behavioral abnormality) of a detection animal. As another example, the system comprises a neurological-based ML-model which analyzes a brain signal from a detection animal. As another example, the system comprises a neurological-based ML-model which predicts a disease state. As another example, the system comprises a neurological-based ML-model which predicts a cancer type. As another example, the system comprises a neurological-based ML-model which predicts a cancer stage. As another example, the system comprises a neurological-based ML-model for verification of a cancer state. As another example, the system comprises a custom ML-model is created for a pack of detection animals. In particular embodiments, the disease-detection system stores one or more black box features to be used in the one or more ML-models. In particular embodiments, the ML-based disease-detection model generates feature representations based on one or more of the behavioral, physiological, neurological data, or patient data.

The aggregations are calculated in multiple aggregative levels. The following list describes example aggregations for dog-round per a specific biological sample. Below, 'X' denotes the dog name, and 'y' the round name:

$$X = \{\text{Pluto, Mars, } \ldots\}$$

$$y = \{\text{main1, main1 + main2, cleaning, lab\_manager, suspicious}\}$$

Features:

1. y_n_X (number of sniffs of dog X at round y)
2. y_sit_X (number of sits of dog X sits at round y)
3. y_sit_prop_X (proportion of sits out of sniffs of dog X at round y)
4. y_multiple_sniffs_sit_n_X (the number of runs with sitting for X,y)
5. y_multiple_sniffs_sit_avg_X (the average number of sniffs per runs with sitting for X,y)
6. y_multiple_sniffs_sit_max_X (the maximum number of sniffs for sitting runs for X,y)
7. y_multiple_sniffs_nosit_n_X, y_multiple_sniffs_nosit_avg_X, y_multiple_sniffs_nosit_max_X (same as above, but for runs without sitting).
8. y_sniff_duration_sit_avg_X, y_sniff_duration_sit_max_X (the average and the maximum duration of a sniff for sniffs with sitting)
9. y_sniff_duration_nosit_avg_X, y_sniff_duration_nosit_max_X (the average and the maximal duration of a sniff for sniffs without sitting)
10. y_sniff2sit_duration_avg_X (average duration between stop sniff to start sit for X,y)
12. y_sniff2sit_duration_max_X (maximal duration between stop sniff to start sit for X,y)

Additional features used in the ML-model are:

12. main1valid_X (indicator for valid main round for dog X)
13. y_is_suspicous (indicator whether the sample was suspicious at round y)
14. lab_result_X
15. Lab_result
16. lab_result_Canine Team Rule
17. Lab_result_Canine Team Rule Model's output:

The ML-model output contains two files:

1. Cancer probability (a scalar between 0 to 1)
2. Predicted confidence interval (a range between 0-1)

Training Overview

Figure 17:
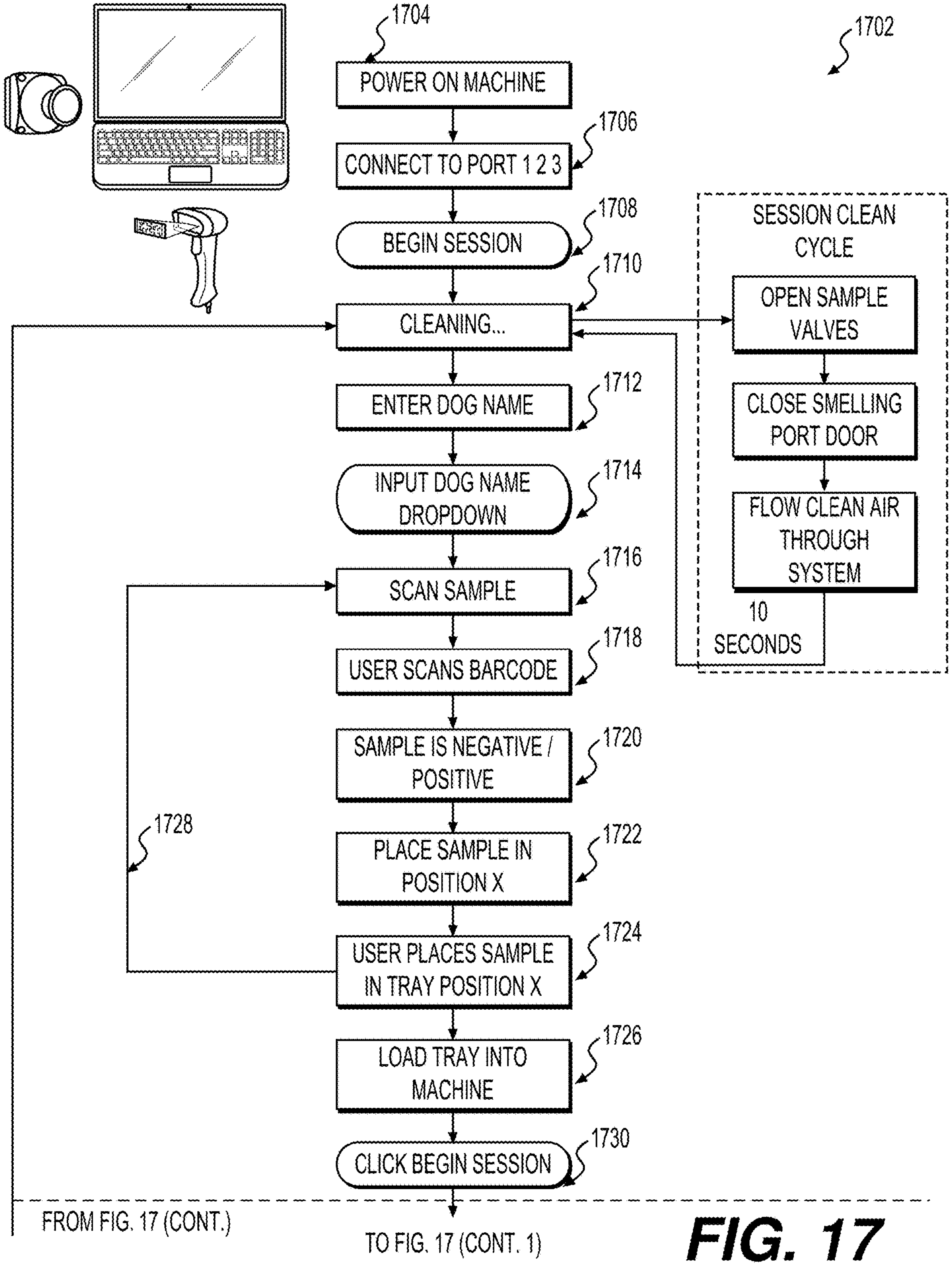
FIG. 17 illustrates a diagram of an example machine-learning (ML) training method.
Figure 17:
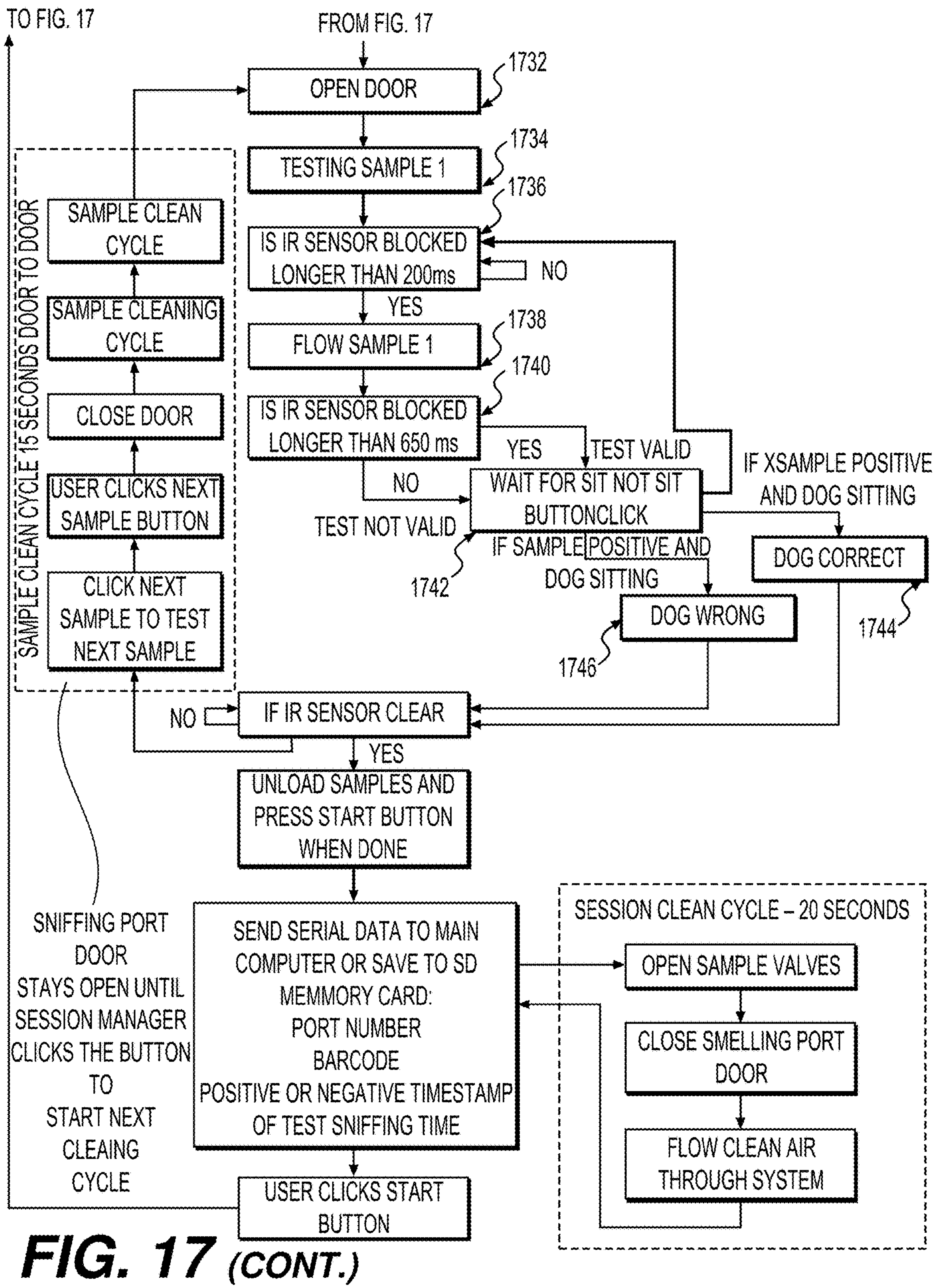

FIG. 17 depicts an example method 1702 for training the ML-based disease-detection model using an olfactometer system. In particular embodiments, the model may be trained in a plurality of aspects, including test management, performance monitoring, and analytics which support training plans.

The method begins at step 1704 wherein the machine is turned on. Then the system connects to a plurality of sample ports at step 1706, and begins a session at step 1708. At step 1710, a clean process is performed to clean the step. An example cleaning procedure for cleaning an olfactometer system is described herein. The cleaning procedure comprises opening the sample valves, closing the sniffing port door, and flowing clean air through the system for a predetermined amount of time (e.g., 10 seconds). At steps 1712 and 1714, a particular detection animal is identified to the model. The identifying information may comprise a name of the detection animal. Next, at step 1716, the user receives an instruction to scan a biological sample for testing, and at step 1718 the user scans the biological sample. Next, the operator (e.g., a lab manager) inputs into the model in indication of whether the sample (e.g. a training sample) is positive or negative for cancer at step 1720. Then, at steps 1722-1726, the sample is placed into position, though the step 1722 comprising placing a sample in position, step 1724 comprising placing the sample in tray position X, and step 1726 comprising loading the tray into the machine. In particular embodiments, the position may be at a particular receptacle in an olfactometer system. In other embodiments, the position may be proximate to a sniffing port. In particular embodiments, the sample is loaded into onto a tray. In certain embodiments, if a user improperly places the sample into position, the system will alert the user and instruct the user to re-perform steps 1716-1724 to properly load the sample into position. Next, at step 1730, a user selects an input which initializes a section. The next steps are depicted on FIG. 17 (Cont.).

After the session as begun, the door to the sniffing port opens at step 1732. Next, at step 1734, the system provides an indicator that testing is active. At step 1736, the system receives data from one or more IR sensors of the sniffing port. The IR sensor measures the length of time a detection animal performs a sniff. In particular embodiments, a sniff of 200 ms constitutes a valid sniff. Upon a determination of a valid sniff of 200 ms or more, the method proceeds to step 1738 wherein a sample is exposed to the detection animal through a flow path. Upon a determination that a sniff was less than 200 ms, the system repeats step 1736 and waits for a new sniff from a detection animal. The system continues to receive data from the IR sensor. At step 1740, the system receives data on whether the IR sensor is blocked for longer than 650 ms. In particular embodiments, if the IR sensor is not blocked for 650 ms, then the sniff is not considered valid. In particular embodiments, if an IR sensor is blocked for 650 ms or more, then the test is considered valid.

At step 1742, the system receives an operator input on whether the detection animal sits. A body pose of a sitting position indicates the presence of cancer in a biological sample. A body pose comprising a standing position indicates that cancer was not detected in the biological sample. The disease state of the training sample (e.g., a biological sample) is known by the lab operator. A user or a machine may input the body pose position of the detection animal so that the ML-based disease-detection model receives information on whether the detection animal correctly identified the sample. If the detection animal makes a correct determination on the state of the sample, then the system provides an indication 1744 that the dog was correct. If the detection animal makes an incorrect determination on the state of the sample, then the system provides an indication 1746 that the dog was wrong. Next, the result, comprising either a dog correct indication 1744 or dog wrong indication 1746, is logged by the system.

Next, at step 1748, the system determines whether the IR sensor detects any obstruction. If the IR sensor is clear, then the system outputs an alert instructing a user to unload the samples. Next, data associated with the test, including the port number, bar code of the sample, a positive or negative detection event, the time of the test, and the sniffing time, are saved in the system. Next, the system may optionally perform a cleaning cycle.

Clinical Validation

Figure 18:
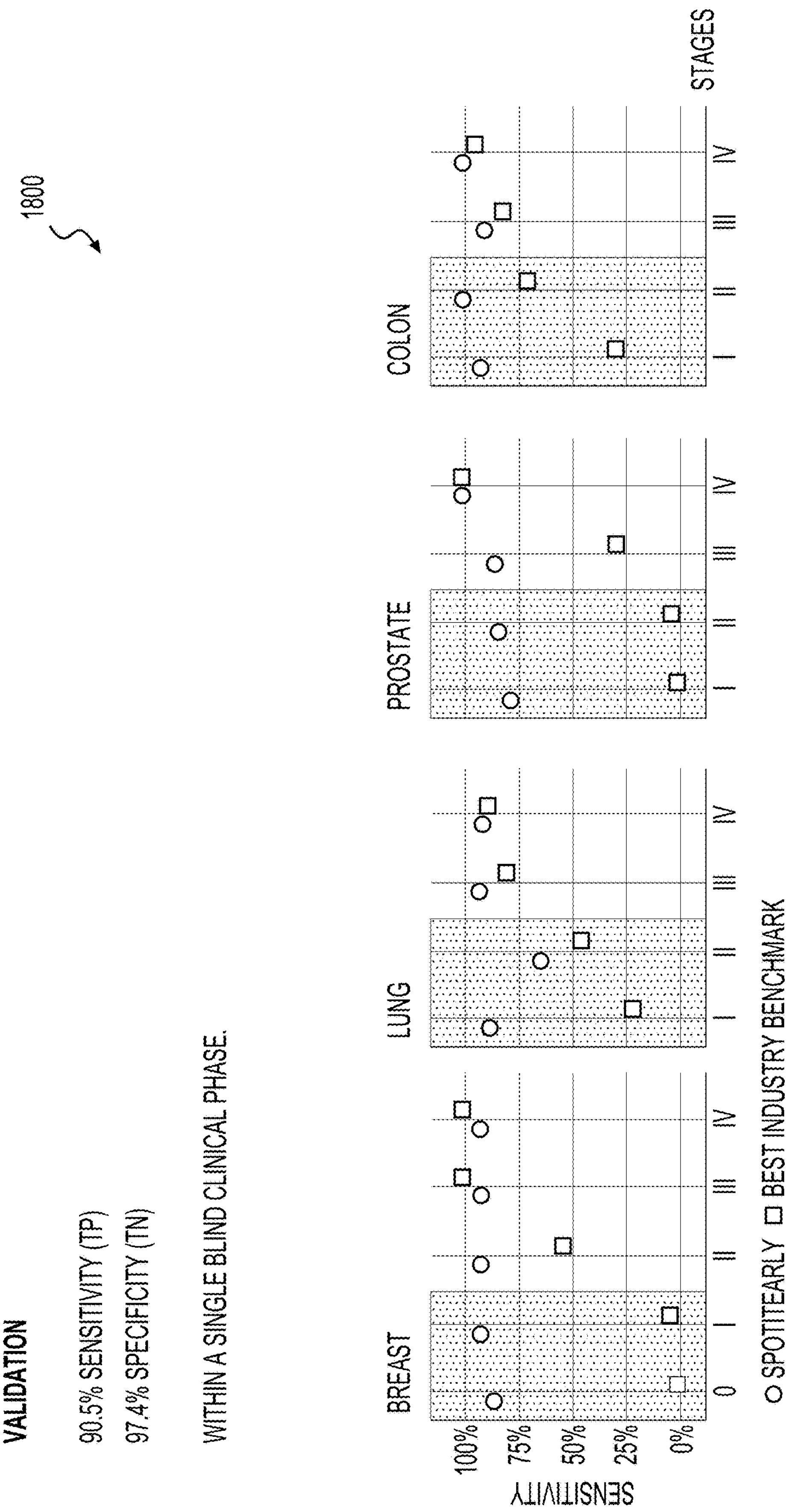
FIG. 18 depicts validation data of the disease-detection method.

FIG. 18 illustrates data 1800 from a single blind clinical phase study which shows that the disclosed systems and methods have been validated by traditional cancer detection methods (e.g. a biopsy) and detects breast, lung, prostate, and colon cancers at similar or better rates compared to traditional industry benchmarks. For instance, the single blind clinical phase study indicated that the disclosed systems and methods have a 90.5% sensitivity rate and a 97.4% specificity rate.

Experimental Results

Figure 19:
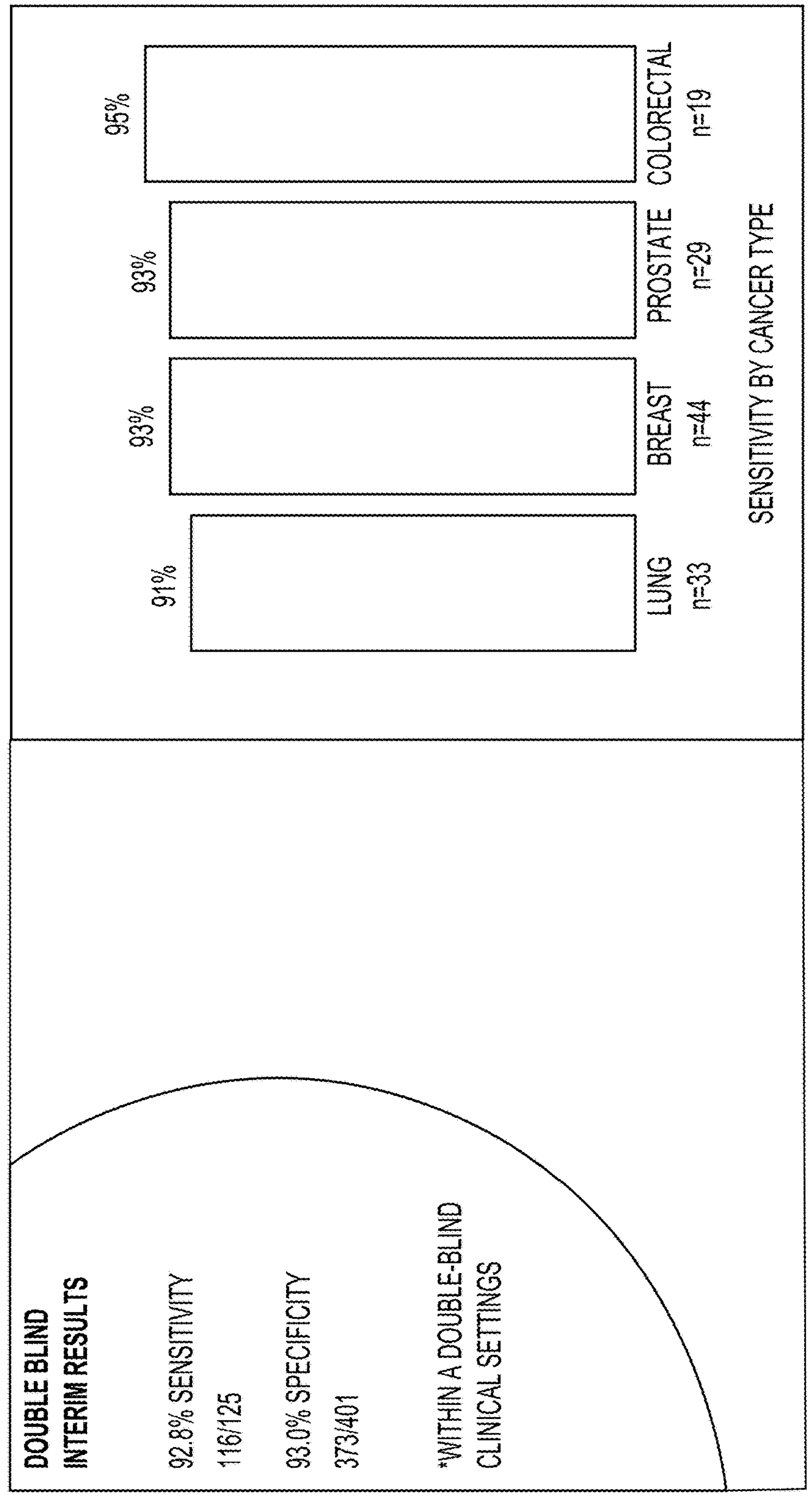
FIG. 19 depicts experimental results.

FIG. 19 illustrates mid-term results 1900 of a double-blind clinical study which was based on a sample of 575 participants that include verified cancer patients—some at a very early stage of the disease—and a control group verified as negative for cancer. The results indicate a 92.8% success rate in identifying the four most common types of cancer—breast, lung, colorectal, and prostate. The disclosed systems and methods show high sensitivity even for early stages, before the appearance of symptoms, which is critical for effective treatment of the disease and saving the patient's life. The data also indicate a low false identification percentage, on the order of 7%. The participants' samples were collected at the hospitals and sent for testing under fully blinded experiment conditions. The survey test was able to identify 92.8% of the sick participants (a particularly high sensitivity compared to the survey measures currently available in the world). The percentage of false positives for the mid-term results was 6.98% (i.e. a test specificity of 93.0%). The test showed stability across the four types of cancer represented in the study: breast cancer, 93%; lung cancer, 91%; colorectal cancer, 95%; and prostate cancer, 93%. Notably, unlike other screening tests that have recently come into use, the high specificity of the disclosed systems and methods have do not come at the expense of sensitivity.

Figure 20:
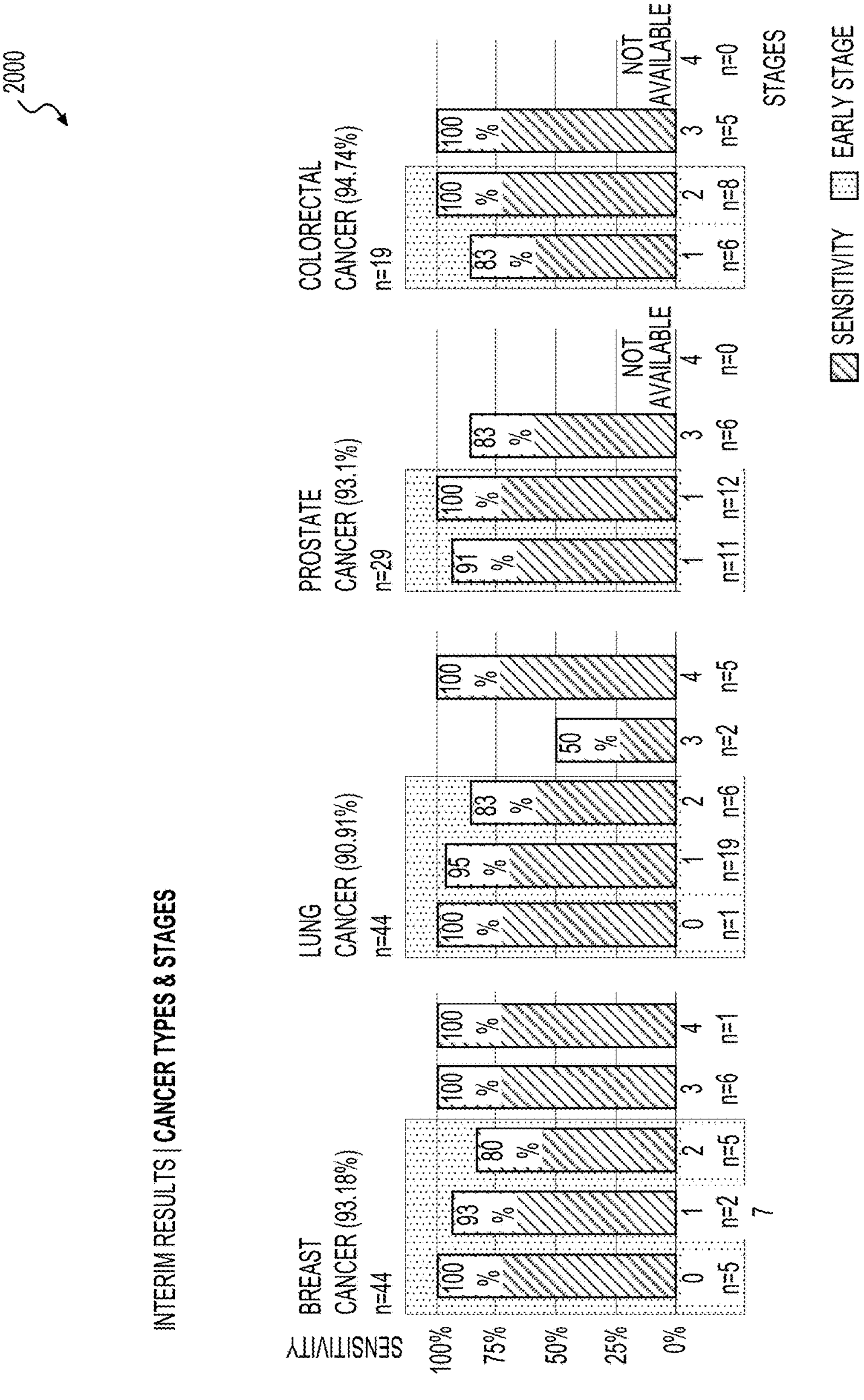
FIG. 20 depicts experimental results.

FIG. 20 illustrates the mid-term results 2000 of the double-blind clinical study based on cancer type and stages. The results are particularly encouraging in light of the fact that the level of test sensitivity remained high even in the early stages of the disease, when symptoms usually do not appear. Detection at these early stages is critical for treatment effectiveness and success. The sensitivity of the test in stage 1 of the tumors was 93% for breast cancer, 95% for lung cancer, 91% for prostate cancer, and 83% for colorectal cancer.

Figure 21:
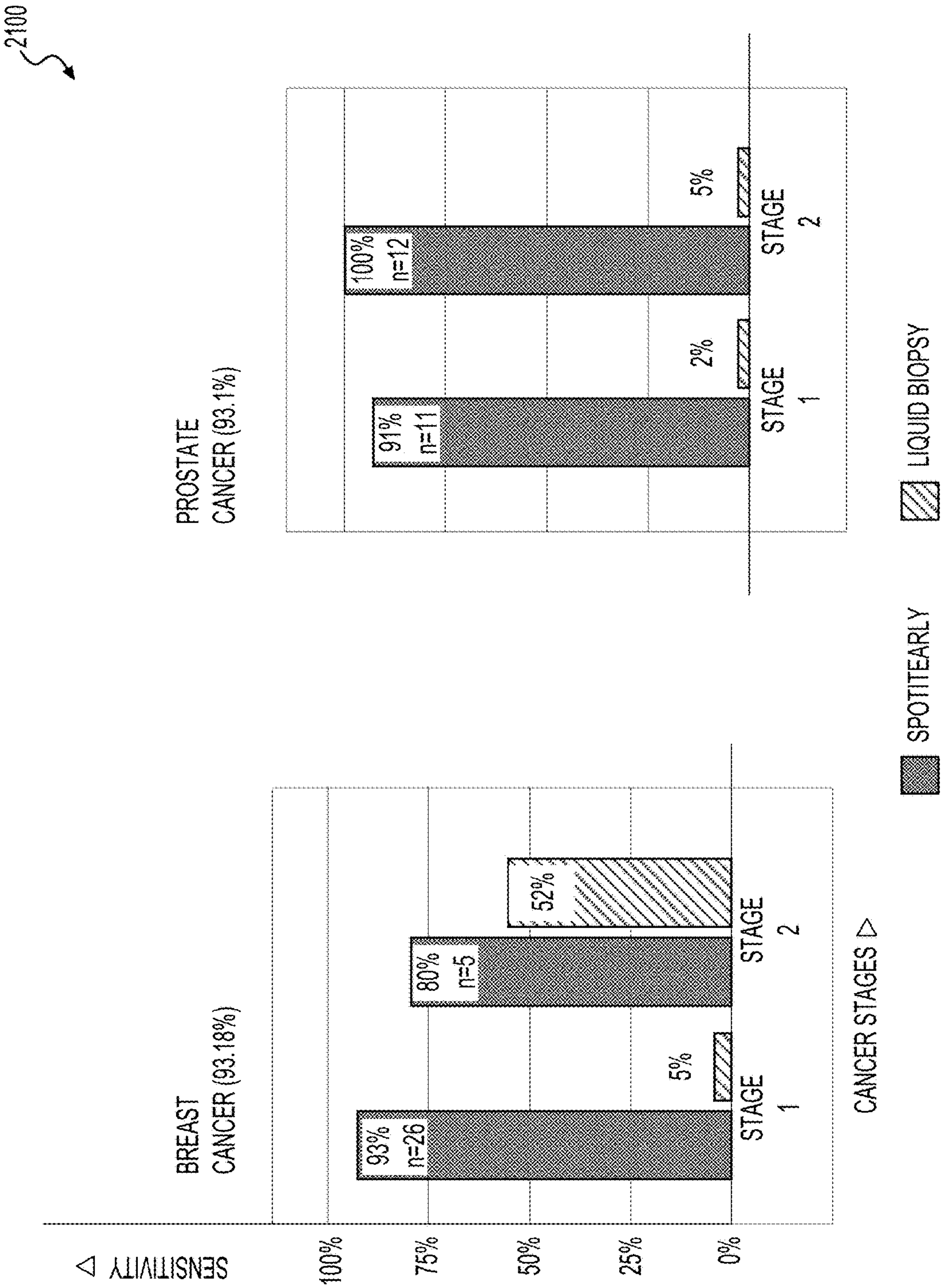
FIG. 21 depicts experimental results.

FIG. 21 illustrates mid-term results 2100 of the double-blind clinical study, and in particular, compares the sensitivity of the present systems and methods with that of a traditional liquid biopsy. The results are highly encouraging in light of the fact that for each type of cancer analyzed, the disclosed systems and methods had a higher sensitivity than a liquid biopsy test at both stage 1 and stage 2 cancer stages.

FIG. 22 illustrates mid-term results 2200 of the double-blind clinical study, and in particular, shows data for certain cancers which the detection animal wasn't specifically trained to detect. In this study, the detection animals were trained to detect breast, lung, prostate, and colorectal cancer. However, the detection animals also detected eight additional cancer types, including, kidney, bladder, ovarian, cervical, stomach, typical carcinoid/endometrial carcinoma, pancreatic/pancreas adenocarcinoma, and vulvar cancers.

Figure 23:
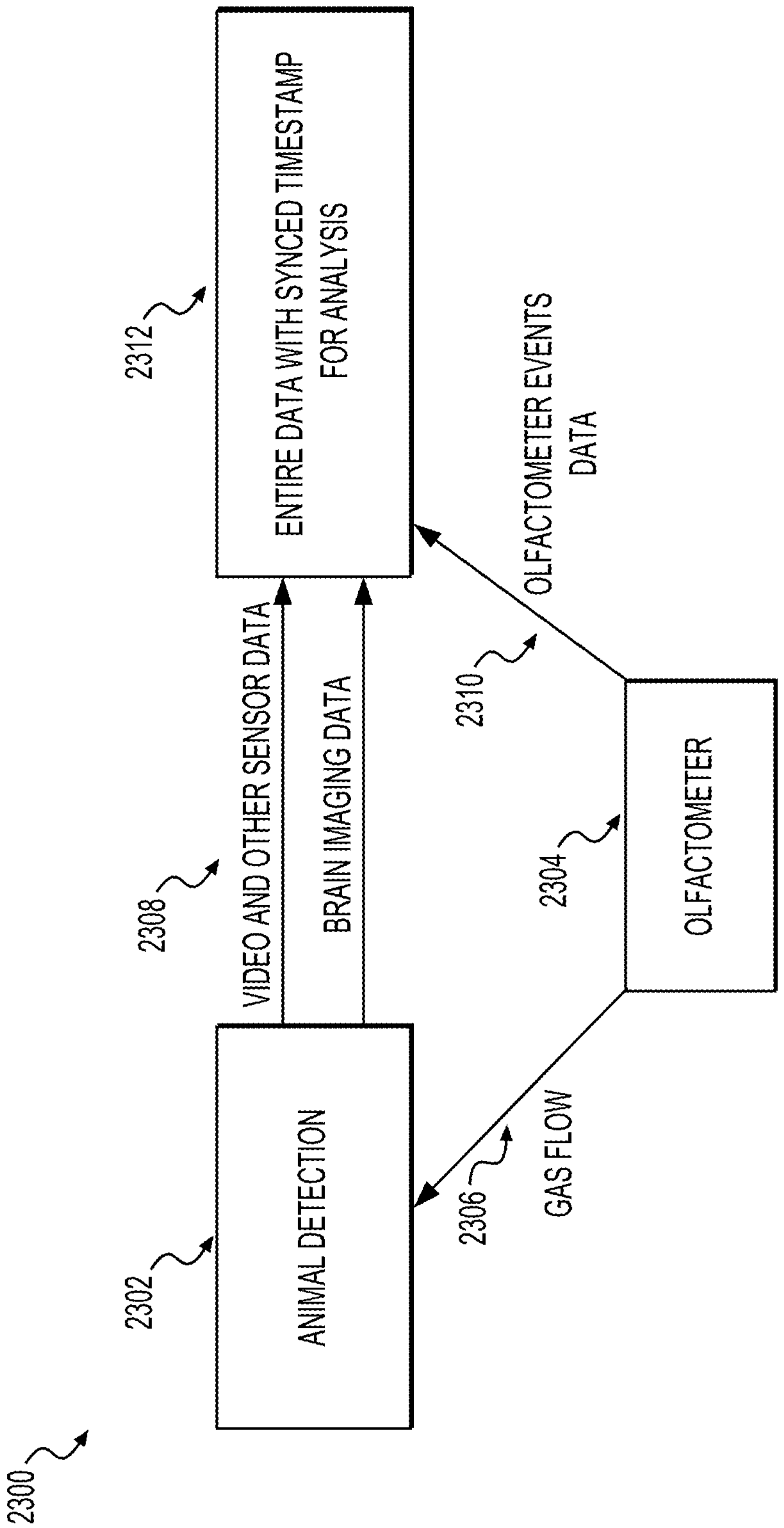
FIG. 23 illustrates an example method utilizing brain imaging.

FIG. 23 depicts an example method 2300 of utilizing brain imaging data for disease-detection. At animal step 2302, one or more detection animals wear a neurological sensor which is operable to gather brain imaging data. For example, the neurological sensor may be an EEG device comprising a plurality of electrodes worn by the detection animal. The animal detection step may further comprise behavioral sensors, such as an accelerometer or gyroscope worn by the detection animal, or an image or audio sensor placed in the test facility. In particular embodiments, the detection animal is exposed to a biological sample via an olfactometer at step 2304. The olfactometer delivers a gas sample to the detection animal, the gas sample comprising VOCs from the biological sample, at step 2306. Optionally, during a control run, the olfactometer delivers a gas sample comprising clean air. That is, the clean air cleans the flow paths and sniffing port. Further, the clean air "re-calibrates" the detection animal by exposing it to an odorless gas. At step 2308, data, including behavioral sensor data, physiological sensor data, and neurological sensor data (e.g., brain imaging data) is streamed to a database. The olfactometer of step 2304 transmits, at step 2310, olfactometer events data. In particular embodiments, the olfactometer events data comprises one or more of a duration of sample exposure, and beginning time of sample exposure, and an ending time of sample exposure. At step 2312, data received from the video/other sensor data and the brain imaging data is synced with the olfactometer events data to form a complete timeline of events for analysis. In particular embodiments, data compiled at step 2312 is input into a neurological-based ML-model for disease-detection. Although this disclosure describes and illustrates particular steps of the method of FIG. 23 as occurring in a particular order, this disclosure contemplates any suitable steps of the method of FIG. 23 occurring in any suitable order. In particular embodiments, neurological testing of the detection animal is performed as a verification step of another test (e.g., a behavioral-based test). In particular embodiments, the verification step confirming the outputted disease state from a prior test. In particular embodiments, the verification step confirming the outputted disease state from a prior test and providing additional information, such as a cancer type or a cancer stage. In particular embodiments, neurological testing of the detection animal is performed as a standalone test capable of detecting one or more of: a cancer state (e.g. a positive or negative state), a cancer type, or a cancer stage.

Figure 24:
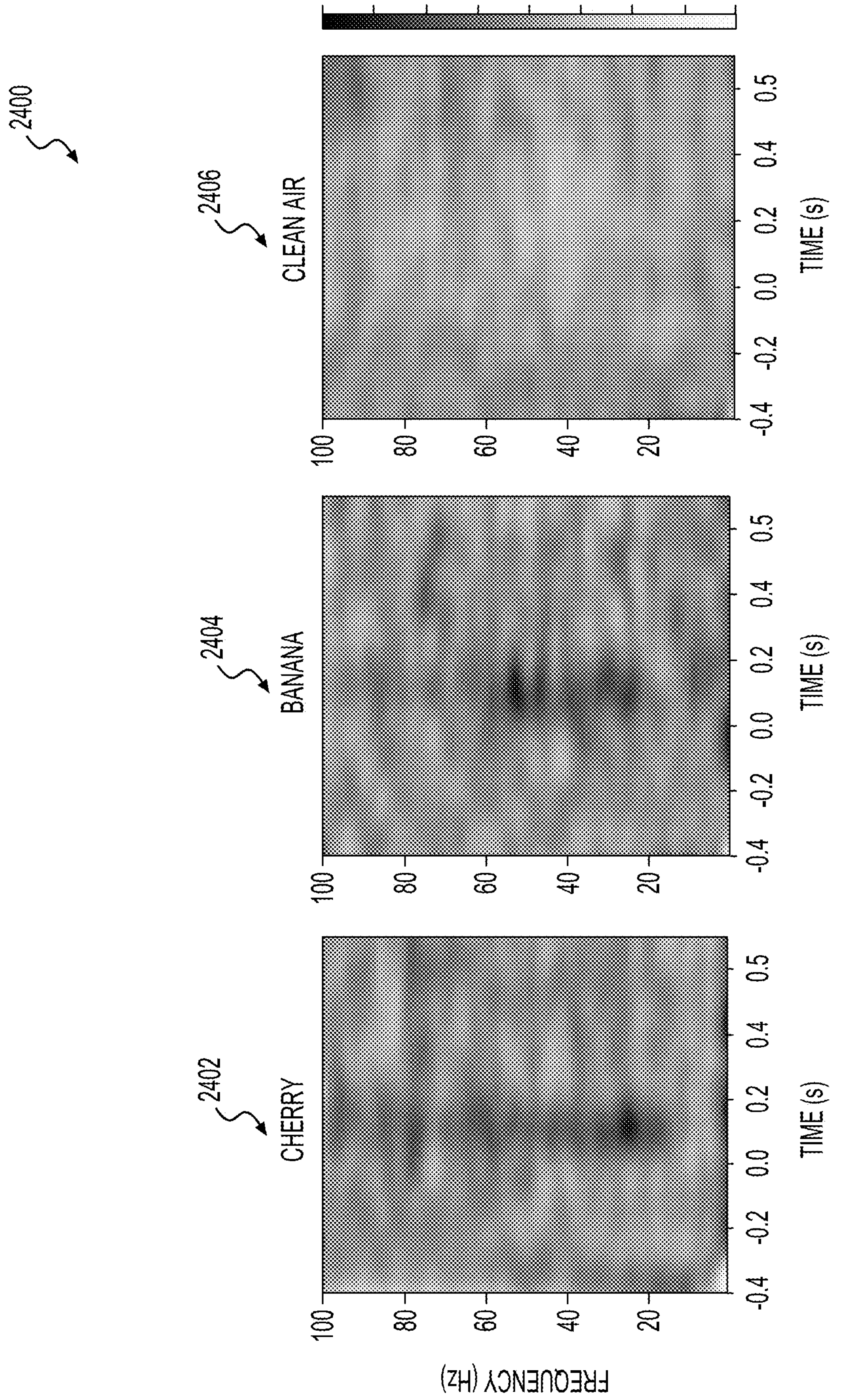
FIG. 24 depicts experimental results utilizing brain imaging.

FIG. 24 depicts an example neurological data 2400 from a canine. The neurological data 2400 comprises the canine's responses to one of an odor of a cherry, banana, or clean air. Graph 2402 characterizes a neurological response to a cherry, graph 2404 characterizes a neurological response to a banana, and graph 2406 characterizes a neurological response to clean air.

Each response 2402, 2404, and 2406 is presented in the frequency domain in different timepoints, thereby reflecting both the frequency and the time domains. The graphs 2402, 2404, and 2406 are based on an aggregation of many exposures of the same sample in the same trial. Each exposure to a target sample (e.g., a cherry, banana, or patient sample) is an "epoch." Between each epoch, clean air is flowed through the olfactometer system, thereby removing the odor from the tubes and recalibrating the canine's olfactory system. While the canine is exposed to the clean air, the EEG continues to record the brain activity, and therefore EEGs from this period reflect the brain activity in a resting state. The EEG data associated with the resting state is used as a baseline for brain activity while the odor exposure.

A detection animal exhibits a different neurological response when exposed to different odors. That is, different odors result in different power values for different frequencies of the EEG measurement as compared to a baseline frequencies' power values of the EEG measurement. The absolute frequency power is obtained from the EEG, and the graphs 2402, 2404, and 2405 present the power values in a representative way. For example: at freq=10 at timepoint 0.2 ms, the power is X. The data is visualized in the graph as:

$$\frac{X-Y}{Y}$$

wherein Y is the average power of freq=10 at the time range before the exposure (e.g., from −0.2 to 0)

Odor exposure occurs at time 0. The power values for each frequency at each time is calculated using Wavelet decomposition (e.g., a Morlet Wavelet).

In particular embodiments, neurological data presented in the manner described herein may be input into a neurological-based ML-model. In particular embodiments, the output of neurological-based ML-model may be input into a container comprising behavioral, physiological data, and/or patient data, wherein data from the container is input into a dog-specific ML-model. In particular embodiments, neurological-based ML-model may function as a standalone test capable of detecting one or more of: a cancer state (e.g. a positive or negative state), a cancer type, or a cancer stage.

Computer System Overview

Figure 25:
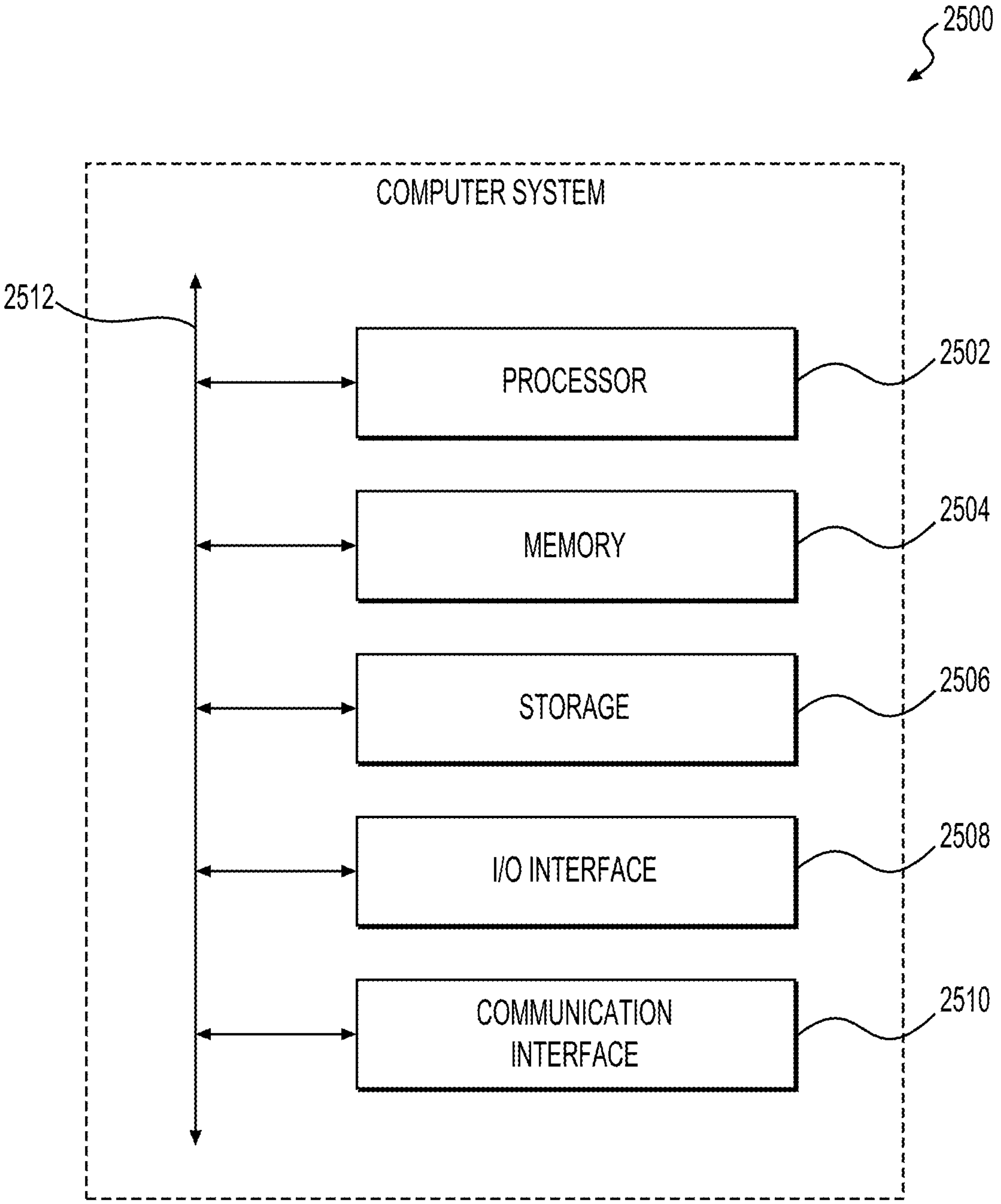
FIG. 25 illustrates an example computer system.

FIG. 25 illustrates an example computer system 2500 that may be utilized to perform a ML-based disease-detection method using detection animals in accordance with the presently disclosed embodiments. In particular embodiments, one or more computer systems 2500 perform one or more steps of one or more methods described or illustrated herein. In particular embodiments, one or more computer systems 2500 provide functionality described or illustrated herein. In particular embodiments, software running on one or more computer systems 2500 performs one or more steps of one or more methods described or illustrated herein or provides functionality described or illustrated herein. Particular embodiments include one or more portions of one or more computer systems 2500. Herein, reference to a computer system may encompass a computing device, and vice versa, where appropriate. Moreover, reference to a computer system may encompass one or more computer systems, where appropriate.

This disclosure contemplates any suitable number of computer systems 2500. This disclosure contemplates computer system 2500 taking any suitable physical form. As example and not by way of limitation, computer system 2500 may be an embedded computer system, a system-on-chip (SOC), a single-board computer system (SBC) (e.g., a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 2500 may include one or more computer systems 2500; be unitary or distributed; span multiple locations; span multiple machines; span multiple data centers; or reside in a cloud, which may include one or more cloud components in one or more networks.

Where appropriate, one or more computer systems 2500 may perform without substantial spatial or temporal limitation one or more steps of one or more methods described or illustrated herein. As an example, and not by way of limitation, one or more computer systems 2500 may perform in real time or in batch mode one or more steps of one or more methods described or illustrated herein. One or more computer systems 2500 may perform at different times or at different locations one or more steps of one or more methods described or illustrated herein, where appropriate.

In particular embodiments, computer system 2500 includes a processor 2502, memory 2504, storage 2506, an input/output (I/O) interface 2508, a communication interface 2510, and a bus 2512. Although this disclosure describes and illustrates a particular computer system having a particular number of particular components in a particular arrangement, this disclosure contemplates any suitable computer system having any suitable number of any suitable components in any suitable arrangement. In particular embodiments, processor 2502 includes hardware for executing instructions, such as those making up a computer program. As an example, and not by way of limitation, to execute instructions, processor 2502 may retrieve (or fetch) the instructions from an internal register, an internal cache, memory 2504, or storage 2506; decode and execute them; and then write one or more results to an internal register, an internal cache, memory 2504, or storage 2506. In particular embodiments, processor 2502 may include one or more internal caches for data, instructions, or addresses. This disclosure contemplates processor 2502 including any suitable number of any suitable internal caches, where appropriate. As an example, and not by way of limitation, processor 2502 may include one or more instruction caches, one or more data caches, and one or more translation lookaside buffers (TLBs). Instructions in the instruction caches may be copies of instructions in memory 2504 or storage 2506, and the instruction caches may speed up retrieval of those instructions by processor 2502.

Data in the data caches may be copies of data in memory 2504 or storage 2506 for instructions executing at processor 2502 to operate on; the results of previous instructions executed at processor 2502 for access by subsequent instructions executing at processor 2502 or for writing to memory 2504 or storage 2506; or other suitable data. The data caches may speed up read or write operations by processor 2502. The TLBs may speed up virtual-address translation for processor 2502. In particular embodiments, processor 2502 may include one or more internal registers for data, instructions, or addresses. This disclosure contemplates processor 2502 including any suitable number of any suitable internal registers, where appropriate. Where appropriate, processor 2502 may include one or more arithmetic logic units (ALUs); be a multi-core processor; or include one or more processors 2502. Although this disclosure describes and illustrates a particular processor, this disclosure contemplates any suitable processor.

In particular embodiments, memory 2504 includes main memory for storing instructions for processor 2502 to execute or data for processor 2502 to operate on. As an example, and not by way of limitation, computer system 2500 may load instructions from storage 2506 or another source (such as, for example, another computer system 2500) to memory 2504. Processor 2502 may then load the instructions from memory 2504 to an internal register or internal cache. To execute the instructions, processor 2502 may retrieve the instructions from the internal register or internal cache and decode them. During or after execution of the instructions, processor 2502 may write one or more results (which may be intermediate or final results) to the internal register or internal cache. Processor 2502 may then write one or more of those results to memory 2504. In particular embodiments, processor 2502 executes only instructions in one or more internal registers or internal caches or in memory 2504 (as opposed to storage 2506 or elsewhere) and operates only on data in one or more internal registers or internal caches or in memory 2504 (as opposed to storage 2506 or elsewhere).

One or more memory buses (which may each include an address bus and a data bus) may couple processor 2502 to memory 2504. Bus 2512 may include one or more memory buses, as described below. In particular embodiments, one or more memory management units (MMUs) reside between processor 2502 and memory 2504 and facilitate accesses to memory 2504 requested by processor 2502. In particular embodiments, memory 2504 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 2504 may include one or more memory devices 2504, where appropriate. Although this disclosure describes and illustrates particular memory, this disclosure contemplates any suitable memory.

In particular embodiments, storage 2506 includes mass storage for data or instructions. As an example, and not by way of limitation, storage 2506 may include a hard disk drive (HDD), a floppy disk drive, flash memory, an optical disc, a magneto-optical disc, magnetic tape, or a Universal Serial Bus (USB) drive or a combination of two or more of these. Storage 2506 may include removable or non-removable (or fixed) media, where appropriate. Storage 2506 may be internal or external to computer system 2500, where appropriate. In particular embodiments, storage 2506 is non-volatile, solid-state memory. In particular embodiments, storage 2506 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 2506 taking any suitable physical form. Storage 2506 may include one or more storage control units facilitating communication between processor 2502 and storage 2506, where appropriate. Where appropriate, storage 2506 may include one or more storages 2506. Although this disclosure describes and illustrates particular storage, this disclosure contemplates any suitable storage.

In particular embodiments, I/O interface 2508 includes hardware, software, or both, providing one or more interfaces for communication between computer system 2500 and one or more I/O devices. Computer system 2500 may include one or more of these I/O devices, where appropriate. One or more of these I/O devices may enable communication between a person and computer system 2500. As an example, and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 2506 for them. Where appropriate, I/O interface 2508 may include one or more device or software drivers enabling processor 2502 to drive one or more of these I/O devices. I/O interface 2508 may include one or more I/O interfaces 2506, where appropriate. Although this disclosure describes and illustrates a particular I/O interface, this disclosure contemplates any suitable I/O interface.

In particular embodiments, communication interface 2510 includes hardware, software, or both providing one or more interfaces for communication (such as, for example, packet-based communication) between computer system 2500 and one or more other computer systems 2500 or one or more networks. As an example, and not by way of limitation, communication interface 2510 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 2510 for it.

As an example, and not by way of limitation, computer system 2500 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 2500 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 2500 may include any suitable communication interface 2510 for any of these networks, where appropriate. Communication interface 2510 may include one or more communication interfaces 2510, where appropriate. Although this disclosure describes and illustrates a particular communication interface, this disclosure contemplates any suitable communication interface.

In particular embodiments, bus 2512 includes hardware, software, or both coupling components of computer system 2500 to each other. As an example, and not by way of limitation, bus 2512 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 2512 may include one or more buses 2512, where appropriate. Although this disclosure describes and illustrates a particular bus, this disclosure contemplates any suitable bus or interconnect.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

Herein, "automatically" and its derivatives means "without human intervention," unless expressly indicated otherwise or indicated otherwise by context.

The embodiments disclosed herein are only examples, and the scope of this disclosure is not limited to them. Embodiments according to the disclosed systems and methods are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A system for disease-detection comprising:

i) an odor-detection system comprising:

a) a sniffing port operably coupled via a flow path to one or more receptacles operable to hold a biological sample of a patient;

b) a means for delivering a predetermined amount of gas from the biological sample from the one or more receptacles to the sniffing port with zero dilution; and c) one or more behavioral sensors proximate to the sniffing port; and ii) a machine learning-based (ML-based) disease-detection model trained on a dataset of detection events, wherein the model is operable to:

receive sensor data associated with one or more detection canines that have been exposed to gas from the biological sample via the sniffing port, wherein the sensor data comprises data received from one or more behavioral sensors which measure one or more of:

a) a duration of a sniff from the detection canines, b) a sniff intensity, c) a number of repeated sniffs, d) a pressure of the detection canine's nose against the sniffing port, or e) auditory features of the sniff;

process the sensor data to generate one or more feature representations; and calculate, based on the one or more feature representations, one or more confidence scores corresponding to one or more disease states associated with the biological sample, wherein each confidence score indicates a probability of the respective disease state being present in the patient and a confidence prediction interval for the respective disease state being present in the patient.

2. The system of claim 1, wherein the sensor data comprises data received from one or more of:

one or more behavioral sensors, one or more physiological sensors, or one or more environmental sensors.

3. The system of claim 2, wherein the one or more behavioral sensors further measure one or more of:

a pose of the detection canine, or whether the detection canine looks at its handler.

4. The system of claim 2, wherein the one or more behavioral sensors comprise one or more of:

one or more audio sensors, one or more image sensors, one or more accelerometers, or one or more pressure sensors.

5. The system of claim 2, wherein the one or more behavioral sensors comprise one or more image sensors that measure one or more of:

the duration of a sniff from the detection canine, a pose of the detection canine, whether the detection canine looks at its handler, or a number of repeated sniffs.

6. The system of claim 2, wherein a length of time between a sniff and a signal from the detection canine indicating a positive disease-detection event is input into the ML-based disease-detection model, wherein the signal comprises one or more of: a pose of the detection canine, the detection canine looking at its handler, or a repeated sniff.

7. The system of claim 2, wherein the one or more physiological sensors comprises one or more of:

one or more heart rate sensors, one or more heart rate variability sensors, one or more temperature sensors, one or more breath rate sensors, one or more sweat rate sensors, one or more galvanic skin response (GSR) sensors, one or more electroencephalogram (EEG) sensors, one or more functional near-infrared spectroscopy (fNIR) sensors, one or more functional magnetic resonance imaging (fMRI) scanners, or one or more magnetic resonance imaging (MRI) scanners.

8. The system of claim 2, wherein the one or more environmental sensors comprise one or more of:

one or more temperature sensors, one or more humidity sensors, one or more audio sensors, one or more gas sensors, or one or more air particulate sensors.

9. The system of claim 1, wherein the ML-based disease-detection model is further operable to:

receive patient data corresponding to the patient, wherein the patient data comprises one or more of:

family medical history, patient medical history, patient age, patient gender, or demographical data.

10. The system of claim 1, wherein the ML-based disease-detection model is further operable to receive data comprising a number of exposures of the detection canine to the biological sample.

11. The system of claim 1, wherein the one or more disease states comprises one or more types of cancer.

12. The system of claim 11, wherein the one or more disease states further comprise one or more stages corresponding to the one or more types of cancer.

13. The system of claim 11, wherein the one or more disease states further comprises one or more sources corresponding to the one or more types of cancer.

14. The system of claim 11, wherein the one or more types of cancer are selected from a group comprising: breast cancer, lung cancer, prostate cancer, and colon cancer.

15. The system of claim 1, wherein the ML-based disease-detection model is trained using a dataset of target odors and detection events, wherein the detection events comprise one or more of canine behaviors, physiological signals, or neurological signals.

16. A method of disease-detection comprising:

receiving a test kit, wherein the test kit comprises a biological sample from a patient;

exposing the biological sample to one or more detection canines via an odor-detection system comprising:

a) a sniffing port operably coupled via a flow path to one or more receptacles operable to hold a biological sample of a patient;

b) a means for delivering a predetermined amount of gas from the biological sample from the one or more receptacles to the sniffing port with zero dilution; and c) one or more behavioral sensors proximate to the sniffing port;

accessing sensor data associated with the detection canines that have been exposed to gas from the biological sample via the sniffing port, wherein the sensor data comprises data received from one or more behavioral sensors which measure one or more of:

a) a duration of a sniff from the detection canines, b) a sniff intensity, c) a number of repeated sniffs, d) a pressure of the detection canine's nose against the sniffing port, or e) auditory features of the sniff;

processing, using a ML-based disease-detection model trained on a dataset of detection events, the sensor data to generate one or more feature representations; and calculating, based on the one or more feature representations, one or more confidence scores corresponding to one or more disease states associated with the biological sample, wherein each confidence score indicates a probability of the respective disease state being present in the patient and a confidence prediction interval for the respective disease state being present in the patient.

17. The method of claim 16, wherein the sensor data comprises data received from one or more of:

one or more behavioral sensors, one or more physiological sensors, or one or more environmental sensors.

18. The method of claim 17, wherein the one or more behavioral sensors further measure one or more of:

a pose of the detection canine; or whether the detection canine looks at its handler.

19. The method of claim 17, wherein one or more behavioral sensors comprise one or more of:

one or more audio sensors, one or more image sensors, one or more accelerometers, or one or more pressure sensors.

20. The method of claim 17, wherein the one or more behavioral sensors comprise one or more image sensors that measure one or more of:

the duration of a sniff from the detection canine, a pose of the detection canine, whether the detection canine looks at its handler, or a number of repeated sniffs.

21. The method of claim 17, wherein a length of time between a sniff and a signal from the detection canine indicating a positive disease-detection event is input into the ML-based disease-detection model, wherein the signal comprises one or more of: a pose of the detection canine, the detection canine looking at its handler, or a repeated sniff.

22. The method of claim 17, wherein the physiological sensor comprises one or more of:

one or more heart rate sensors, one or more heart rate variability sensors, one or more temperature sensors, one or more breath rate sensors, one or more sweat rate sensors, one or more galvanic skin response (GSR) sensors, one or more electroencephalogram (EEG) sensors,
one or more functional near-infrared spectroscopy (fNIR) sensors,
one or more functional magnetic resonance imaging (fMRI) sensors, or
one or more magnetic resonance imaging (MRI) sensors.

23. The method of claim 17, wherein the one or more environmental sensors comprise one or more of:
one or more temperature sensors,
one or more humidity sensors,
one or more audio sensors,
one or more gas sensors, or
one or more air particulate sensors.

24. The method of claim 16, wherein the ML-based disease-detection model receives patient data, wherein the patient data includes or more of:
family medical history,
patient medical history,
patient age,
patient gender, or
demographical data.

25. The method of claim 16, wherein the ML-based disease-detection model receives data comprising a number of exposures of the detection canine to the biological sample.

26. The method of claim 16, wherein the one or more disease states comprises one or more types of cancer.

27. The method of claim 26, wherein the one or more disease states further comprise one or more stages corresponding to the one or more types of cancer.

28. The method of claim 26, wherein the one or more disease states further comprises one or more sources corresponding to the one or more types of cancer.

29. The method of claim 26, wherein the one or more types of cancer are selected from a group comprising: breast cancer, lung cancer, prostate cancer, and colon cancer.

30. The method of claim 16, wherein the ML-based disease-detection model is trained using a dataset of target odors and detection events, wherein the detection events include animal behavior, physiological signals, or neurological signals.

* * * * *